(12) United States Patent
Bostwick et al.

(10) Patent No.: US 12,263,219 B2
(45) Date of Patent: Apr. 1, 2025

(54) THERAPEUTIC COMPOSITION AND METHOD COMBINING MULTIPLEX IMMUNOTHERAPY WITH CANCER VACCINE FOR THE TREATMENT OF CANCER

(71) Applicant: Rampart Health, L.L.C., Orlando, FL (US)

(72) Inventors: David Granger Bostwick, Orlando, FL (US); Brian Rafferty Bostwick, Orlando, FL (US); Peter John Littrup, Bloomfield Hills, MI (US)

(73) Assignee: Rampart Health, L.L.C., Orlando, FL (US)

( * ) Notice: Subject to any disclaimer, the term of this patent is extended or adjusted under 35 U.S.C. 154(b) by 0 days.

(21) Appl. No.: 17/670,146

(22) Filed: Feb. 11, 2022

(65) Prior Publication Data
US 2022/0257761 A1 Aug. 18, 2022

Related U.S. Application Data

(60) Provisional application No. 63/148,922, filed on Feb. 12, 2021.

(51) Int. Cl.

| | | |
|---|---|---|
| A61K 39/395 | (2006.01) | |
| A61B 18/02 | (2006.01) | |
| A61K 9/00 | (2006.01) | |
| A61K 31/675 | (2006.01) | |
| A61K 38/19 | (2006.01) | |
| A61K 38/20 | (2006.01) | |
| A61K 38/21 | (2006.01) | |
| A61K 39/00 | (2006.01) | |
| A61K 45/06 | (2006.01) | |
| A61P 35/04 | (2006.01) | |

(52) U.S. Cl.
CPC ........ *A61K 39/39558* (2013.01); *A61B 18/02* (2013.01); *A61K 9/0019* (2013.01); *A61K 31/675* (2013.01); *A61K 38/191* (2013.01); *A61K 38/193* (2013.01); *A61K 38/2026* (2013.01); *A61K 38/204* (2013.01); *A61K 38/208* (2013.01); *A61K 38/212* (2013.01); *A61K 38/217* (2013.01); *A61K 39/0011* (2013.01); *A61K 45/06* (2013.01); *A61P 35/04* (2018.01); *A61K 2039/507* (2013.01); *A61K 2039/5152* (2013.01)

(58) Field of Classification Search
None
See application file for complete search history.

(56) References Cited

U.S. PATENT DOCUMENTS

2016/0243231 A1* 8/2016 Har-Noy ............... A61K 39/39
2021/0154281 A1* 5/2021 Irvine .................... A61K 35/17

FOREIGN PATENT DOCUMENTS

WO WO-2015168379 A2 * 11/2015 ......... A61K 39/0011
WO WO 2020/178775 * 9/2020

OTHER PUBLICATIONS

Johnson et al (JAMA Oncology, 2019, 5:999-1007).*
Deacon et al (BMC Cancer, 2008, 8:630, p. 1-11).*
Gershan et al (Journal for Immuno Therapy of Cancer, 2015, 3:24, internet pp. 1-11).*
Chen et al (Cellular & Molecular Immunology, 2013, 10:349-359).*
Har-Noy (US Patent Application Publication 2016/0243231).*
Skye, H.M., Pfotenhauer, J.M. ((2020). Chapter 2: Joule Thomson Cryocoolers and Cryoablation. In: Atrey, M. (eds) Cryocoolers. International Cryogenics Monograph Series. Springer, Cham).*
Waitz et al (Cancer Research, 2012, 72:430-439).*
Kang et al (Biomaterials, 2018, 164:80-97).*
Cancer.gov National Cancer Institute (printed Aug. 2023).*
Mkrtichyan et al (Eur. J. Immunol. 2011, 41:2977-2986).*
Berd et al (Cancer Investigation, 1988, 6:337-349).*
Boerrigter et al (Immunopharmacology, 1986, 11:13-20).*
Rotte (Journal of Experimental & Clinical Cancer Research, 2019, 38:255, internet pp. 1-12).*
Duraiswamy et al (Cancer Research, 2013, 73:3591-3603).*
Van Elsas et al (Journal of Experimental Medicine, 1999, 190:355-366).*
Soares et al (Journal of Immunotherapy, 2015, 38:1-11).*
ClinicalTrials.gov NCT04274816 (posted Feb. 2020; 7 pages).*
Walter et al (Oncoimmunology, 2013, 2:1, e22246).*
Le et al (Cancer Research, 2012; 72:3439-3444).*
Powell et al (Lung Cancer, 2006, 52:189-197).*
Yatim et al (Science, 2015, 350:328-334).*
Hanna (Human Vaccines & Immunotherapeutics 2012, 8:1156-1160).*
Rocconi et al (Journal of Clinical Oncology, 2020, 38, 15_suppl. Abstract 3002).*
Gerritsen et al (Journal of Clinical Oncology, 2007, 25:No. 18_suppl. Abstract 5120).*
Wright et al (J Immunoology, 2020, 204 (1_Suppl):241:23, abstract).*
https://www.cancer.gov/about-cancer/treatment/types/surgery/cryosurgery (printed Mar. 2024).*
Li et al., "Allogeneic GM-CSF-secreting tumor cell immunotherapies generate potent anti-tumor responses comparable to autologous tumor cell immunotherapies," Clinical Immunology, vol. 133, No. 2, (Nov. 1, 2009), pp. 184-197.
Duraiswamy et al., "Dual Blockade of PD-1 and CTLA-4 Combined with Tumor Vaccine Effectively Restores T-Cell Rejection Function in Tumors," American Association for Cancer Research, vol. 73, No. 12, (Jun. 15, 2013), pp. 3591-3603.

(Continued)

*Primary Examiner* — Laura B Goddard
(74) *Attorney, Agent, or Firm* — Jeffrey N. Townes; Cozen O'Connor

(57) ABSTRACT

This invention relates to a therapeutic composition comprising i) at least two immune checkpoint inhibitors, ii) at least one drug selected from a cytokine a cytotoxic or cytostatic chemotherapeutic drug, and combinations thereof, and iii) a cancer vaccine prepared from tumor or cancer cells, or derivatives thereof, that have been prepared through an ex vivo treatment that creates necrotic and/or necroptotic cancer cells while minimizing destruction of cancer antigens. This invention also relates to a method of treating a tumor or a cancer in a patient comprising administering to a patient in need thereof the therapeutic composition in an amount effective to treat the tumor or cancer.

18 Claims, No Drawings

(56) References Cited

OTHER PUBLICATIONS

Srivatsan et al., "Allogeneic tumor cell vaccines: The promise and limitations in clinical trials," Human Vaccines & Immunotherapeutics, vol. 10, No. 1, (Sep. 24, 2013), pp. 52-63.

Wei et al., "Combinatorial PD-1 Blockade and CD137 Activation Has Therapeutic Efficacy in Murine Cancer Models and Synergizes with Cisplatin," PLOS One, vol. 8, No. 12, (Dec. 19, 2013), pp. e84927.

Zheng et al., "812 Urelumab (Anti-CD137 Agonist) in Combination with Vaccine and Nivolumab Treatments is Safe and Associated with Pathologic Response as Neoadjuvant and Adjuvant Therapy for Resectable Pancreatic Cancer," J Immunother Cancer, (Nov. 1, 2020), pp. A485-A486.

Muth et al., "CD137 agonist-based combination immunotherapy enhances activated, effector memory T cells and prolongs survival in pancreatic adenocarcinoma," Cancer Letters, vol. 499, (Nov. 30, 2020), pp. 99-108.

Cui et al., "TLRs as a Promise Target Along With Immune Checkpoint Against Gastric Cancer," Frontiers in Cell and Developmental Biology, vol. 8, (Jan. 5, 2021), pp. 611444.

Seymour, "Urelumab Combo Leads to Improved Pathologic Response in Resectable PDAC," Targeted Therapies in Oncology, vol. 10, No. 1, (Jan. 25, 2021), pp. 1-12.

\* cited by examiner

THERAPEUTIC COMPOSITION AND METHOD COMBINING MULTIPLEX IMMUNOTHERAPY WITH CANCER VACCINE FOR THE TREATMENT OF CANCER

This application claims priority to U.S. Provisional Application No. 63/148,922, filed on Feb. 12, 2021, which is herein incorporated by reference in its entirety.

FIELD OF THE INVENTION

This invention relates to therapeutic compositions combining immunologic and chemotherapeutic methods and cancer vaccines for the treatment of cancer.

BACKGROUND

Cancer is the second most common cause of death in the US, claiming 580,000 Americans per year, more than 1,500 people each day. The National Institutes of Health (NIH) estimated the overall annual costs of cancer care at more than $227 billion (in 2007); including $89 billion for direct medical costs. Much of the overall healthcare costs of treating cancer are derived from management of the deleterious side effects of radiation and conventional chemotherapy.

Multiple therapies have been used for metastatic solid cancer that vary according to site and histologic types of cancers (e.g., squamous cell carcinoma, urothelial carcinoma, adenocarcinoma, sarcoma, lymphoma, melanoma, etc.), including chemotherapy, immunotherapy, surgery, external beam radiation therapy, brachytherapy, manipulation therapy such as cryosurgery, and hormonal therapy (for certain cancers). Many of these therapies confer a survival benefit, which, however, needs be weighed against the incidence of significant adverse events in this population.

For instance, immunologic cancer treatment is poised to completely change the landscape of oncologic therapeutics. Checkpoint inhibitors, such as CTLA-4 and PD-1, are already making a major impact in the treatment of metastatic melanoma and non-small cell lung cancer. These drugs are now being used in combination in an attempt to improve their efficacy. The delivery of these drugs is commonly performed intravenously which can have serious and sometimes fatal systemic toxicities as a result of nonspecific distribution of these cytocidal agents in the body, which kill both cancer cells and normal cells and can negatively impact the treatment regimen and patient outcome.

Manipulation is a surgical technique used to selectively injure or destroy cells, organs, or abnormal growths (such as cancers). Cryosurgical freezing has been known to elicit an immune response in patients through the presentation of a unique array of tumor associated antigens to a patient's antigen presenting cells and dendritic cells. This "cryoimmunologic effect", however, has been known to be variable and in some instances even detrimental.

WO 2017/123981 relates to a pharmaceutical composition comprising at least two immune checkpoint inhibitors and at least one cytokine, and its combination with a manipulation step. Cytokine is a naturally-occurring protein that is secreted by cells of the immune system or non-immune cells (e.g. epithelial cells) in response to a number of stimuli and assist in regulating the development of immune effector cells. Cytokine is an immunomodulation agent that acts through a mechanism that ultimately alters gene expression in the target cells. The combination of the two immune checkpoint inhibitors and a cytokine is within the regime of immunotherapy by using exclusive immunologic agents.

Many efforts at cancer immunotherapy to date have focused on the mechanism of action of drugs, with less regard for the process and mechanism of cancer antigen release and presentation. Cancer vaccines often focus on a single antigen without considering the likelihood of adaptability of cancer in response to the threat posed by attack on only one antigen. After the entire payload of tumor associated antigens (TAAs) is released from cancer cells, neighboring immature dendritic cells can be activated and begin the process of identifying other intact cancer cells elsewhere in the body that express the same antigens, recruiting cytotoxic T-cells that then surround and destroy the cancer.

The adaptive immune system, while the primary mediator of tumor rejection, also plays a protective role in the growth of human cancers. Consequently, efforts have been made to control or blunt this response to allow maximum immune destruction of cancer cells by using an immunotherapeutic antibody to inactivate $T_{Reg}$ cells and prolong this inactivation. This ensures that the cytotoxic T-cell cancer cell destruction does not self-abort prematurely. However, these therapeutic methods focus on only one of the cancer antigens.

In addition to those subjects diagnosed at late stages of cancer, those who fail primary therapy for localized cancer may progress, and in some cases reach metastatic status. For example, in the case of metastatic prostate cancer, androgen deprivation therapy is the standard treatment and achieves temporary control or regression in the great majority of subjects, based on serum PSA levels and radiographic assessment. However, many subjects with metastatic prostate cancer eventually undergo disease progression while on this therapy, thereby reaching a state of metastatic androgen-independent prostate cancer.

Several therapeutic cancer vaccines are available or being evaluated in clinical trials, including autologous dendritic cells pulsed with prostatic acid phosphatase (see Harzstark et al., "Immunotherapy for prostate cancer using antigen-loaded antigen-presenting cells: APC8015 (Provenge)," *Expert Opin Biol Ther.* 7(8):1275-1280 (2007)); whole allogeneic cell lines transfected to secrete GM-CSF (see Small et al., "Granulocyte macrophage colony-stimulating factor—secreting allogeneic cellular immunotherapy for hormone-refractory prostate cancer," *Clin Cancer Res.* 13(13): 3883-3891 (2007)); and recombinant attenuated vaccinia virus engineered to express prostate-specific antigen and three immune co-stimulatory molecules, ICAM-1, B7.1, and lymphocyte function-associated antigen-3 (see Doehn et al., "Drug evaluation: Therion's rV-PSA-TRICOM+rF-PSA-TRICOM prime-boost prostate cancer vaccine," *Curr Opin Mol Ther.* 9(2):183-189 (2007)). Several therapeutic vaccine approaches have been discussed (see Sonpavde et al., "Vaccine therapy for prostate cancer. *Urol Oncol.* 25(6):451-459 (2007); Slovin, "Emerging role of immunotherapy in the management of prostate cancer," *Oncology (Williston Park)* 21(3):326-333; discussion 334, 338, 346-348 (2004); Karnes et al., "Immunotherapy for prostate cancer," *Curr Pharm Des.* 2(7):807-817 (2006); Ragde et al., "Dendritic cell based vaccines: progress in immunotherapy studies for prostate cancer," *J Urol.* 172 (6 Pt 2):2532-2538 (2004)). For instance, for prostate cancer, the Sipuleucel-T clinical trial employed DC as cellular adjuvants loaded with recombinant antigen—PAP and PSMA respectively—to induce to a mature phenotype prior administration. Results from these and other DC immunotherapy trials have yielded a specific immune response, resulting in a mean of 4 months of life extension (e.g., for Sipuleucel-T). However, these therapies typically cost more than $100,000, and patients could still die soon thereafter. These findings indicate that current immunotherapeutic treatments are of limited value for the majority of patients.

Adjuvants or other modalities have been added to cancer vaccines to enhance antigen recognition and T-cell activation, and may include one or more of the following: 1) genetic or chemical modification of cell-based vaccines; 2) cross-priming tumor-associated antigens to T-cells by engaging dendritic cells; 3) T-cell adoptive therapy; 4) stimulation of cytotoxic inflammation by non-specific immunomodulators, toll-like receptor agonists, cytokines, chemokines or hormones; 5) reduction of immunosuppression and/or stimulation of antitumor effector cells using antibodies, small molecules; and 6) various cytostatic or cytoreductive modalities, including chemotherapy. However, current technologies combining cancer vaccines with these modalities have not reached their full clinical potential, at least partly due to its toxicity and the difficulty in mounting a significant anti-cancer response in subjects, because of pre-existing tolerance mechanisms that actively turn off immune recognition and/or disable effector T-cells in the tumor microenvironment.

There thus remains a need in the art to develop an improved method to not only reduce the toxicities associated with traditional systemic cancer treatments but also provide an optimal cancer immune response for an improved treatment of cancers. This disclosure answers that need.

SUMMARY OF THE INVENTION

One aspect of the invention relates to a therapeutic composition, comprising: i) at least two immune checkpoint inhibitors, ii) at least one drug selected from a cytokine, a cytotoxic or cytostatic chemotherapeutic drug, and combinations thereof, and iii) a cancer vaccine prepared from tumor or cancer cells, or derivatives thereof, that have been prepared through an ex vivo treatment that creates necrotic and/or necroptotic cancer cells while minimizing destruction of cancer antigens. Optionally, the therapeutic composition can comprise a pharmaceutically acceptable carrier.

Another aspect of the invention relates to a method of treating a tumor or a cancer comprising: administering to the subject a therapeutic composition comprising: i) at least two immune checkpoint inhibitors, ii) at least one drug selected from a cytokine, a cytotoxic or cytostatic chemotherapeutic drug, and combinations thereof, and iii) a cancer vaccine prepared from tumor or cancer cells, or derivatives thereof, that have been prepared through an ex vivo treatment that creates necrotic and/or necroptotic cancer cells while minimizing destruction of cancer antigens, in an amount effective to treat the tumor or cancer.

Additional aspects, advantages and features of the invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of the stated aspects, advantages and features make up the inventions disclosed in this application.

DETAILED DESCRIPTION OF THE INVENTION

The present disclosure is based, at least in part, on the development of new compositions and methods to elicit a cancer immune response through a combination of tumor-directed immunologic cancer treatments and cancer vaccines prepared through an ex vivo treatment such as a manipulation technique.

The inventors have discovered an approach that combines an ex vivo created (e.g., via UV irradiation and/or other manipulations) cancer vaccine (e.g., autologous) with multiple check point inhibitors and a cytokine or low-dose chemotherapeutic agent to harness additive or synergistic mechanisms of systemic cancer killing while minimizing antagonistic interactions and adverse events. The therapeutic compositions and treatment methods described in this invention can exploit all of the cancer antigens—not just one— that are present throughout the specific patient's cancer (personalized cancer treatment) by releasing innumerable antigens with carefully controlled induction of necrosis and necroptosis to balance the need for cell destruction with that of structural preservation and release of antigens.

The term "ex vivo" means that the treatment of the cancer specimen (e.g., by manipulation or manipulations that may also include irradiation) takes place outside the patient under more controlled conditions than is possible with in vivo treatments (in the patient) at the expense of altering the "natural" environment. A primary advantage of using ex vivo tissues or cells is the ability to perform treatments (e.g., manipulation/irradiation) or tests that would otherwise be complicated and risky in living subjects (e.g., damage of vital structures and exposure to spinal or general anesthesia). Tissues or cells may be removed in many ways, including in part, as whole organs, or as larger organ system.

Ex vivo treatment of cancer obtained from tissue specimens and subsequent administration of such ex vivo created cancer vaccine may have significant advantages over traditional systemic delivery of anti-cancer drugs. The therapeutic compositions and treatment methods disclosed herein can allow for smaller-than-traditional doses to be administered to the subject (e.g., in the embodiments where the therapeutic compositions are administered directly into the skin), a stimulation of the immune system against the tumor antigens, and improved results by placing the drugs and the tumor antigens in proximity to the immune inflammatory process. Ex vivo treatment can avoid the need for systemic (general) anesthesia during the treatment, can avoid the need for treatment equipment, such as cryosurgical or other manipulative equipment, to be used in contact with the patient (thereby lowering manipulation-induced risks), and can decrease the length of time needed for each treatment.

By comparison, many other methods of cell destruction that use heat, such as microwave and HIFU (high intensity focused ultrasound), denature antigenic proteins, altering the antigens from their natural state and rendering them unable to act as accurate signals for cancer antigen targets on other cancer cells.

This difference in antigen handling, provided by the therapeutic compositions and treatment methods described herein, can ensure that antigens are fully exposed and preserved without denaturation, allowing targeting and activation of immature dendritic cells with patient-specific and cancer-specific antigens that can be identified at metastatic sites.

The inventors surprisingly discovered that, by using the combination of immune checkpoint inhibitors, cytokines or cytotoxic or cytostatic chemotherapeutic drugs, and cancer vaccine derived from ex vivo-treated-cancer (obtained from tissue specimens, e.g., biopsies, resections, aspirations, etc.), the treatment method provided at least the following benefits, including: (1) soft tissue injection of multiplex combination immunotherapy combined with ex vivo treatment allows for a low-dose (lower than traditional doses) immunotherapy; (2) the side effect profile of low-dose immunotherapy is more favorable and exposes patients to fewer risks than traditional dosing; (3) preserving cancer neo-antigens by employing no or minimal thermal destruction (e.g., no or minimal thermal manipulation); and (4) lower complications and risks than conventional in vivo treatment (e.g., ex vivo manipulation rather than in vivo manipulation).

Additionally, the approach described here is beneficial because it can

- ensure that a full range, or at least a broader range, of patient-specific and cancer-specific antigens are exposed to the immune system. This is unlike the current cancer vaccines (e.g., Provenge for prostate cancer) which recognize a single pre-determined cancer antigen that may or may not be expressed by a patient's cancer;
- maximize, or at least increase, the quantity and quality of the exposed tumor antigens by using a specialized method that induces necrosis and necroptosis without significantly denaturing these proteins (because, if denatured, they will not work as well) and preserve the blood vasculature to allow entry and egress of the immune system dendritic and cytotoxic T-cells;
- utilize the natural range of co-stimulators in the cancer lysate induced by necrosis or necroptosis in combination with the inflammatory environment;
- create close proximity of tumor antigens and the inflammatory immune process by injecting the cancer lysate and medications intra-dermally or intra-tumorally;
- allow for a targeted personalized vaccine by destroying cancer cells and releasing the entire repertoire, or at least a large number, of cancer-specific antigens, rather than focusing one or a few pre-selected antigens.

In one aspect, the present disclosure provides a therapeutic composition for tumor or cancer treatment comprising, consisting essentially of, or consisting of, a combination of i) at least two immune checkpoint inhibitors, ii) at least one drug selected from a cytokine, a cytotoxic or cytostatic chemotherapeutic drug, and combinations thereof, and iii) a cancer vaccine prepared from tumor or cancer cells, or derivatives thereof, that have been prepared through an ex vivo treatment that kills cancer cells (e.g., creates necrotic and/or necroptotic cancer cells) while minimizing destruction of cancer antigens. Optionally, the therapeutic composition can comprise a pharmaceutically acceptable carrier.

Immune checkpoint inhibitors are a type of drug that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Checkpoint inhibitors therefore work to activate the immune system to attack tumors, inhibiting the immune response proteins responsible for down regulating the immune system. Such checkpoint inhibitors may include small molecule inhibitors or may include antibodies, or antigen binding fragments thereof, that bind to and block or inhibit immune checkpoint receptors or antibodies that bind to and block or inhibit immune checkpoint receptor ligands.

For instance, PD-1 and CTLA-4 attenuate T-cell activity through independent molecular mechanisms. See Das et al., "Early B cell changes predict autoimmunity following combination immune checkpoint blockade." *J Clin Invest.* 128(2):715-720 (2018); Das et al., "Combination therapy with anti-CTLA-4 and anti-PD-1 leads to distinct immunologic changes in vivo." *J Immunol.* 194(3):950-959 (2015), which are incorporated by reference in their entirety. The enhanced benefit of combination checkpoint inhibitor blockade is likely mediated by multiple mechanisms distinct from the component monotherapies rather than by additive engagement of the cellular and molecular mechanisms of each monotherapy. See Wei et al., "Fundamental Mechanisms of Immune Checkpoint Blockade Therapy. *Cancer Discov.*" 8(9):1069-1086 (2018), which is incorporated by reference in its entirety. It is possible that positive co-stimulation by blockade beyond physiologic levels facilitates acquisition of enhanced cytolytic capabilities or novel properties not displayed by canonical T-cell populations, resulting in enhanced efficacy. Little has been known of the relative contribution for each of the several known molecular mechanisms of PD-1 and CTLA-4 blockade to therapeutic efficacy. Combination checkpoint inhibitor blockade therapy can improve therapeutic efficacy compared with monotherapy in both preclinical and clinical studies. See Curran et al., "PD-1 and CTLA-4 combination blockade expands infiltrating T cells and reduces regulatory T and myeloid cells within B16 melanoma tumors." *Proc Natl Acad Sci USA.* 107(9):4275-4280 (2010); Postow et al., "Immunologic correlates of the abscopal effect in a patient with melanoma." *New England Journal of Medicine.* 366(10):925-931 (2012); Wolchok et al., "Ipilimumab monotherapy in patients with pretreated advanced melanoma: a randomised, double-blind, multicentre, phase 2, dose-ranging study." *Lancet Oncol.* 11(2):155-164 (2010), which are incorporated by reference in their entirety. Patients with metastatic melanoma treated by combination therapy with PD-1 and CTLA-4 blockade may achieve responses in 36% and greater than 50% in some instances, with 57% 3-year overall survival. See Larkin et al., "Combined Nivolumab and Ipilimumab or Monotherapy in Untreated Melanoma." *N Engl J Med.* 373(1):23-34 (2015), which is incorporated by reference in its entirety. Combination therapy may also produce overall survival benefit in metastatic renal cell carcinoma when compared with standard-of-care. See Motzer et al., "Nivolumab plus Ipilimumab versus Sunitinib in Advanced Renal-Cell Carcinoma." *N Engl J Med.* 378(14):1277-1290 (2018), which is incorporated by reference in its entirety.

The checkpoint inhibitors comprise inhibitors such as inhibitors of CD137 (4-1BB); CD134; PD-1; KIR; LAG-3; PD-L1; PDL2; CTLA-4; B7 family ligands such as B7.1 (or CD80) or B7.2 (or CD86), B7-DC, B7-H1, B7-H2, B7-H3 (or CD276), B7-H4, B7-H5, B7-H6 and B7-H7; BTLA (or CD272); LIGHT; HVEM; GALS; TIM-3; TIGHT; VISTA; 2B4; CGEN-15049; CHK1; CHK2; A2aR; TGF-β; PI3Kγ; GITR; ICOS; IDO; TLR; IL-2R; IL-10; PVRIG (B7/CD28); CCRY; OX-40; CD160; CD20; CD52; CD47; CD73; CD27-CD70; and CD40.

Suitable CD137 (4-1BB) inhibitors include, but are not limited to, utomilumab, urelumab, or a combination thereof. Suitable CD134 or OX40 inhibitors include, but are not limited to, OX40-immunoglobulin (OX40-Ig), GSK3174998 (an anti-OX40 antibody), 9B12, MOXR 0916, PF-04518600 (PF-8600), MEDI6383, MEDI0562, INCAGN01949, or a combination thereof. Suitable KIR inhibitors include, but are not limited to, IPH4102, 1-7F9 (a human monoclonal antibody that binds KIR2DL1/2L3), lirilumab, or a combination thereof. Suitable LAG-3 inhibitors include, but are not limited to, relatlimab, IMP321 (Immuntep®), GSK2831781 (an agonist antibody to LAG3), BMS-986016, LAG525, or a combination thereof.

Suitable CTLA-4 inhibitors include, but are not limited to, ipilimumab, tremelimumab, or a combination thereof. Suitable PD-1 inhibitors include, but are not limited to, pembrolizumab, nivolumab, pidilizumab, MK-3475, MED 14736 (a monoclonal antibody), CT-011, spartalizumab, or a combination thereof. Suitable PD-L1 or PD-L2 inhibitors include, but are not limited to durvalumab, atezolizumab, avelumab, AMP224, BMS-936559, MPLDL3280A (an anti-PD-L1 antibody), MSB0010718C (an anti-PD-L1 antibody), or a combination thereof. Suitable B7.1 (or CD80) or B7.2 (or CD86) inhibitors include, but are not limited to, rhudex, abatacept, or a combination thereof. Suitable B7-H3 inhibitors include, but are not limited to, enoblituzumab (MGA271), MGD009, 8H9 (a monoclonal antibody to B7-H3), or a combination thereof. Suitable CD20 inhibitors include, but are not limited to rituximab, ofatumumab, or a combination thereof. Suitable CD52 inhibitors include, but are not limited to alemtuzumab. Suitable CD47 inhibitors include, but are not limited to, Hu5F9-G4, TTI-621 (SIRPαFc), or a combination thereof. Suitable CD73 inhibitors include, but are not limited to, MEDI9447. Suitable CD27-CD70 inhibitors include, but are not limited to, ARGX-110, BMS-936561 (MDX-1203), varlilumab, or a combination thereof. Suitable CD40 inhibitors include, but are not limited to, CP-870893, APX005M, ADC-1013, JNJ-64457107, SEA-CD40, R07009789, or a combination thereof.

Suitable BTLA (or CD272) inhibitors include, but are not limited to 40E4; 40E4 mIgG1; D265A, or a combination thereof. Suitable LIGHT (or CD272) inhibitors include, but are not limited to T5-39; 17-2589-42 (a CD258 (LIGHT) monoclonal antibody), TNFSF14, or a combination thereof. Suitable HVEM inhibitors include, but are not limited to anti-CD270. Suitable TIM-3 inhibitors include, but are not limited to MBG453, MEDI9447, or a combination thereof. Suitable TIGHT inhibitors include, but are not limited to, OMP-31M32. Suitable VISTA inhibitors include, but are not limited to, JNJ-61610588, CA-170, or a combination thereof. Suitable CGEN-15049 inhibitors include, but are not limited to, anti-CGEN-15049. Suitable A2aR inhibitors include, but are not limited to, CPI-444. Suitable TGF-β inhibitors include, but are not limited to, trabedersen (AP12009), M7824, galusertinib (LY2157299), or a combination thereof. Suitable PI3Kγ inhibitors include, but are not limited to, IPI-549. Suitable GITR inhibitors include, but are not limited to, TRX-518, BMS-986156, AMG 228, MEDI1873, MEDI6469, MK-4166, INCAGN01876, GWN323, or a combination thereof. Suitable ICOS inhibitors include, but are not limited to, JTX-2011, GSK3359609, MEDI-570, or a combination thereof. Suitable IDO inhibitors include, but are not limited to, BMS-986205, indoximod, epacadostat, or a combination thereof. Suitable TLR inhibitors include, but are not limited to, MEDI9197, PG545 (pixatimod, pINN), polyinosinic-polycytidylic acid polylysine, carboxymethylcellulose (poly-ICLC), or a combination thereof. Suitable IL-2R inhibitors include, but are not limited to, NKTR-214. Suitable IL-10 inhibitors include, but are not limited to, AM0010. Suitable PVRIG (B7/CD28) inhibitors include, but are not limited to, COM701.

Additional checkpoint inhibitors suitable for use herein also include those described in Marin-Acevedo et al., "Next generation of immune checkpoint therapy in cancer: new developments and challenges," *Journal of Hematology & Oncology* 11:39 (2018), which is incorporated herein by reference in its entirety.

The therapeutic composition can comprise any combination of two or more check point inhibitors. They may be the same type of checkpoint inhibitors or they may be different checkpoint inhibitors. In some embodiments, the at least two checkpoint inhibitors comprise a CTLA-4 inhibitor and a PD-1 inhibitor. In some embodiments, the at least two checkpoint inhibitors comprise a CTLA-4 inhibitor and a PD-L1 inhibitor. In some embodiments, the CTLA-4 inhibitor is ipilimumab and the PD-1 inhibitor is pembrolizumab.

A skilled practitioner would appreciate that many other combinations of the checkpoint inhibitors are also suitable for the therapeutic composition. A non-limiting list of the combinations include a CD137 inhibitor and a CD134 inhibitor; a PD-1 inhibitor and a KIR inhibitor; a LAD-3 inhibitor and a PD-L1 inhibitor; a CTLA-4 inhibitor and a CD40 inhibitor; a CD 134 inhibitor and a PD-1 inhibitor; a KIR inhibitor and a LAG-3 inhibitor; a PD-L1 inhibitor and a CTLA-4 inhibitor; a CD40 inhibitor and a CD 137 inhibitor; a CTLA-4 inhibitor and a PD-L1 inhibitor; a PD-1 inhibitor and a CD40 inhibitor; or any other combinations of two or more of the checkpoint inhibitors known in the art.

The therapeutic compositions can also comprise at least one drug selected from a cytokine, a cytotoxic or cytostatic chemotherapeutic drug, and combinations thereof.

The drug can be a cytokine drug. The term "cytokine" refers to a large group of cellular protein components or a drug that can be secreted by specific cells of the immune system that mediate cell signaling and regulate immunity, inflammation and hematopoiesis.

Suitable cytokines include, but are not limited to, erythropoietin, G-CSF, GM-CSF, IL-2, IL-4, IL-6, IL-12, TNF, interferons such as INF-α-2a, INF-α-2b, INF-0, and INF-γ, or a combination thereof. In one embodiment, the cytokine is GM-CSF.

Alternatively, the drug can be a cytotoxic or cytostatic chemotherapeutic drug. The term "cytotoxic" or "cytostatic" refers to a cellular component or a drug that can cause the inhibition of cell growth and multiplication of cancer cells or cause cancer cells to die.

Suitable cytotoxic or cytostatic chemotherapeutic drugs include, but are not limited to, actinomycin, aldesleukin, alemtuzumab, alitretinoin, altretamine, amsacrine, anastrozole, arsenic trioxide, asparaginase, azacitidine, azathioprine, *Bacillus* calmette-geurin vaccine (BCG), bevacizumab, bexarotene, bicalutamide, bleomycin, bortezomib, botulinum toxin (Botox), busulfan, capecitabine, carboplatin, carmustine, cetrorelix acetate, cetuximab, chlorambucil, chloramphenicol, chlormethine hydrochloride, choriogonadotropin alfa, ciclosporin, cidofovir, cisplatin, cladribine, clofarabine, clorambucil, colchicine, crisantaspase, cyclophosphamide, cytarabine, dacarbazine, dactinomycin, danazol, dasatinib, daunorubicin HCl, decitabine, denileukin, dienostrol, diethylstilbestrol, dinoprostone, dithranol-containing products, docetaxel, doxorubicin, dutasteride, epirubicin, ergometrine/methylergometrine, estradiol, estramustine phosphate sodium, estrogen-progestin combinations, conjugated estrogens, esterified estrogens, estrone, estropipate, etoposide, exemestane, finasteride, floxuridine, fludarabine, fluorouracil, fluoxymesterone, flutamide, fulvestrant, ganciclovir, ganirelix acetate, gemcitabine, gemtuzumab ozogamicin, gondaotrophin, chorionic goserelin (zoladex), hydroxycarbamide, ibritumomab tiuxetan, idarubicin, ifosfamide, imatinib mesilate, interferon Alfa-2b, interferon-containing products, irinotecan HCl, leflunomide, letrozole, leuprorelin acetate, lomustine, lymphoglobuline, medroxyprogesterone, megestrol, melphalan, menotropins, mercaptopurine, mesena, methotrexate, methyltestosterone, mifepristone, mitomycin, mitotane, mitoxantrone HCl, mycophenolate, mofetil, nafarelin, natalizumab, nilutamide, oestrogen-containing products, oxaliplatin, oxytocin (including syntocinon and syntometrine), paclitaxel, paraldehyde, pegaspargase, pemetrexed disodium, pentamidine isethionate, pentostatin, perphosphamide, pipobroman, piritrexim isethionate, plicamycin, podofilox, podophyllin, *Podophyllum* resin, prednimustine, procarbazine, progesterone-containing products, progestins, raloxifene, raltitrexed, ribavirin, rituximab, sirolimus, streptozocin, tacrolimus, tamoxifen, temozolomide, teniposide, testolactone, testosterone, thalidomide, thioguanine, thiotepa, thymoglobulin, tioguanine, topotecan, toremifene citrate, tositumomab, trastuzumab, treosulfan, tretinoin, trifluridine, trimetrexate glucoronate, triptorelin, uramustine, vaccines (live), valganciclovir, valrubicin, vidarabine, vinblastine sulfate, vincristine, vindesine, vinorelbine tartrate, zidovudine, or a combination thereof.

Exemplary cytotoxic or cytostatic chemotherapeutic drugs are asparaginase, bleomycin, busulphan, carboplatin, cetuximab, cisplatin, cyclophosphamide, BCG, chloramphenicol, colchicine, cyclosporin, dacarbazine, doxorubicin, etoposide, fludarabine, gemcitabine, ifosfamide, irinotecan, lomustin, melphalan, methotrexate, mitomycinmitoxantrone, paclitaxel, procarbazine, rituximab, temozolomide, thitepa, vinblastine, vincristine, zidovudine, and a combination thereof. In one embodiment, the cytotoxic or cytostatic chemotherapeutic drug is cyclophosphamide.

The combination of two or more check point inhibitors with a cytokine is different than the combination of two or more check point inhibitors with a chemotherapeutic agent (cytostatic or cytotoxic), such as cyclophosphamide. And the combination of two or more check point inhibitors with a chemotherapeutic agent (cytostatic or cytotoxic) is different than the combination of two or more check point inhibitors with another immunotherapeutic agent, such as a cytokine. Fundamentally, the drug classes for and mechanism of action in the polypharmacy combinations of the latter combination differ from those of the former combination. In particular, chemotherapeutic agents are usually anti-metabolites and are synthetic drugs, not protein drugs, whereas cytokines are naturally-occurring proteins and are considered biologics. Although both classes of these agents have pleiotropic effects on the immune system, the repertoire of effects and the mechanisms of actions to induce these effects are markedly different for these two different classes of agents. Additionally, the mechanism of suppression of cytokines (suppressor of cytokine signaling proteins) differs from that of chemotherapeutic drugs.

Cytokines are low molecular weight regulatory proteins or glycoproteins that are usually secreted by cells of the immune system or non-immune cells (e.g. epithelial cells) in response to a number of stimuli and assist in regulating the development of immune effector cells. Cytokines bind to the specific receptors on the membrane of target cells, triggering signal transduction pathways that ultimately alter gene expression in the target cells. The actions of cytokines are involved in a wide range of biological processes.

On the other hand, chemotherapeutic agents may promote cancer immunity by inducing immunogenic cell death directly or indirectly. Direct actions of chemotherapy include induction of necroptosis or autophagy. Indirect actions include altering cell signaling pathways, thwarting efforts used by cancer to avoid immune modulation (see Emens et al., "Chemotherapy: friend or foe to cancer vaccines?" *Curr Opin Mol Ther.* 3(1):77-84 (2001), which is incorporated herein by reference in its entirety); release and enhancement of presentation of cancer neoantigens and danger-associated molecular patterns (DAMP), such as, for example, when chemokine signaling by CXCL8 stimulates dendritic cell identification and consumption of injured cancer cells by exposing calreticulin on the cell surfaces (see Sukkurwala et al., "Immunogenic calreticulin exposure occurs through a phylogenetically conserved stress pathway involving the chemokine CXCL8." *Cell Death Differ.* 21(1): 59-68 (2014), which is incorporated herein by reference in its entirety); enhancement of effector T-cell activity by upregulating MHC class 1 expression, costimulatory molecules such as B7-1, or the cancer neoantigens themselves; or by downregulating coinhibitory molecules such as PD-L1/B7-H1 or B7-H4 (see Chen et al., "Chemoimmunotherapy: reengineering tumor immunity." *Cancer Immunol Immunother.* 62:203-216 (2013), which is incorporated herein by reference in its entirety). Chemotherapy-induced T-cell mediated killing of cancer may involve fas-, perforin-, and Granzyme B-dependent mechanisms. See Chen et al., "Chemoimmunotherapy: reengineering tumor immunity." *Cancer Immunol Immunother.* 62:203-216 (2013), which is incorporated herein by reference in its entirety.

Cytostatic and cytotoxic chemotherapeutic agents alone have shown dose-dependent effects on the immune system. See Emens, "Chemoimmunotherapy." *Cancer J* 16:295-303 (2010); Chen et al., "Chemoimmunotherapy: reengineering tumor immunity." *Cancer Immunol Immunother* 62:203-216 (2013), which are incorporated by reference in their entirety.

The chemotherapeutic agents have been used to regulate cancer immunity while avoiding the toxicity associated with higher doses required for direct cell killing. This modulation has been demonstrated with several chemotherapeutic agents, such as cyclophosphamide, paclitaxel, cisplatin, and temozolomide. For example, cyclophosphamide has shown pleiotropic immune-modulating properties, including, e.g., depleting Tregs. See Machiels et al., "Cyclophosphamide, doxorubicin, and paclitaxel enhance the antitumor immune response of granulocyte/macrophage-colony stimulating factor-secreting whole-cell vaccines in HER-2/neu tolerized mice." *Cancer Res.* 61(9):3689-3697 (2001), which is incorporated by reference in its entirety. Taxanes such as paclitaxel may also deplete Tregs, facilitate dendritic cell maturation, and shift the CD4+ T-helper phenotype from type 2 to type 1, resulting in enhanced proinflammatory cytokine secretion and priming and lytic activity of CD8+ T cells. Doxorubicin may delay tumor outgrowth and enhance vaccine activity, although the mechanism of this immunomodulation is uncertain. Combination of cyclophosphamide and doxorubicin have also shown favorable effect, curing some mice of cancer with selective depletion of Tregs, allowing recruitment of high-avidity cancer-specific T cells. Combination of a HER2 ♭, GM-CSF-secreting breast cancer vaccine, with immune-modulating doses of cyclophosphamide and doxorubicin, may selectively deplete CD4+ Tregs relative to effector T cells, activating effector T cells. See "Immediate versus deferred treatment for advanced prostatic cancer: initial results of the Medical Research Council Trial. The Medical Research Council Prostate Cancer Working Party Investigators Group." *Br J Urol.* 79(2):235-246 (1997), which is incorporated by reference in its entirety. Other chemotherapeutic agents, such as gemcitabine, have also shown effects on the immune system, including induction of apoptosis, promotion of dendritic cell cancer antigen presentation, and facilitation of cross-priming of CD8+ T cells. See Nowak et al., "Induction of tumor cell apoptosis in vivo increases tumor antigen cross-presentation, cross-priming rather than cross-tolerizing host tumor-specific CD8

T cells." *J Immunol.* 170(10):4905-4913 (2003), which is incorporated by reference in its entirety.

The combination of two or more check point inhibitors with a cytokine or a chemotherapeutic agent (cytostatic or cytotoxic) may benefit from targeting other non-redundant aspects of the cancer-immunity life cycle such as novel molecules, tissue site of action, immune cell population, and biological process. For example, VISTA, a molecule from the immunoglobulin superfamily (IgSF), is expressed primarily on M2 macrophages following ipilimumab (anti-CTLA-4) treatment in patients with metastatic prostate cancer. See Gao et al., "VISTA is an inhibitory immune checkpoint that is increased after ipilimumab therapy in patients with prostate cancer. *Nat Med.* 2017; 23(5):551-555, which is incorporated by reference in its entirety. VISTA and PD-1 have non-redundant inhibitory effects on T cells. See Liu et al., "Immune-checkpoint proteins VISTA and PD-1 nonredundantly regulate murine T-cell responses." *Proc Natl Acad Sci USA.* 112(21):6682-6687 (2015), which is incorporated by reference in its entirety. As another example, gemcitabine can enhance the efficacy of a dendritic cell-based vaccine by increasing T-cell trafficking and sensitizing tumor cells to T cell-mediated lysis in a murine pancreatic cancer model. See Bauer et al., "Concomitant gemcitabine therapy negatively affects DC vaccine-induced CD8(+) T-cell and B-cell responses but improves clinical efficacy in a murine pancreatic carcinoma model." *Cancer Immunol Immunother.* 63(4):321-333 (2014), which is incorporated by reference in its entirety. In a phase II clinical trial of patients with metastatic renal cell carcinoma, An additional example is [0040] the use of cyclophosphamide and multipeptide vaccine IMA901, which can improve survival in those who developed multipeptide immune responses, suggesting a diverse tumor-specific immune response generated by multiple antigens. See Walter et al., "Multipeptide immune response to cancer vaccine IMA901 after single-dose cyclophosphamide associates with longer patient survival." *Nat Med.* 18(8):1254-1261 (2012), which is incorporated by reference in its entirety.

Certain trials in patients with non-small-cell lung cancer and melanoma have showed that combinations of chemotherapy with ipilimumab could be safe (see Weber et al. "Randomized phase I pharmacokinetic study of ipilimumab with or without one of two different chemotherapy regimens in patients with untreated advanced melanoma," Cancer Immunology 13:7 (2013), which is incorporated by reference in its entirety). However, there were also reports of an increase in specific adverse effects such as transaminitis, probably owing to intravenous administration (see Robert et al., "Ipilimumab plus dacarbazine for previously untreated metastatic melanoma. *New England Journal of Medicine* 11; 364(26):2517-26 (2011), which is incorporated by reference in its entirety).

Factors such as dose, treatment schedule, route of administration, etc., may contribute to minimizing toxicity. Data, however, are very limited on the efficacy of combining an immune checkpoint blockade with a cytokine or a low-dose chemotherapeutic agent. The combination of two or more check point inhibitors with a cytokine or a low-dose chemotherapeutic agent (cytotoxic or cytostatic) could harness additive or synergistic mechanisms of systemic cancer killing while minimizing antagonistic interactions and adverse events.

In some embodiments, the drug in the therapeutic compositions can comprise a combination of a cytokine and a cytotoxic or cytostatic chemotherapeutic drug.

In some embodiments, the drug in the therapeutic composition comprises a cytokine drug, and the therapeutic composition can further comprise a second cytokine. The second cytokine drug can be the same as or different from the first cytokine drug.

In some embodiments, the drug in the therapeutic composition comprises a cytotoxic or cytostatic chemotherapeutic drug, and the therapeutic compositions can further comprise a second cytotoxic or cytostatic chemotherapeutic drug. The second cytotoxic or cytostatic chemotherapeutic drug can be the same as or different from the first cytotoxic or cytostatic chemotherapeutic drug.

The immune checkpoint inhibitors are present in the therapeutic composition in a therapeutically effective amount. For instance, the concentration of each immune checkpoint inhibitor may range from about 0.1 to about 500 mg/ml, for instance from about 0.1 to about 300 mg/ml, from about 0.1 to about 200 mg/ml, from about 0.1 to about 100 mg/ml, from about 0.5 to about 100 mg/ml, from about 0.5 to about 50 mg/ml, from about 0.5 to about 30 mg/ml, from about 0.5 to about 20 mg/ml, from about 0.5 to about 10 mg/ml, from about 1 to about 10 mg/ml, from about 1 to about 5 mg/ml, or from about 1 to about 2 mg/ml.

The cytokine drugs or cytotoxic or cytostatic chemotherapeutic drugs, if present, are also present in the therapeutic composition in a therapeutically effective amount.

For instance, the concentration of each cytokine drug may range from about 1 μg/ml to about 1000 mg/ml, from about 1 to about 1000 mg/ml, from about 1 to about 500 mg/ml, from about 10 to about 500 mg/ml, from about 50 to about 500 mg/ml, from about 100 to about 500 mg/ml, from about 1 μg/ml to about 50 mg/ml, from about 1 μg/ml to about 30 mg/ml, from about 1 μg/ml to about 20 mg/ml, from about 1 μg/ml to about 10 mg/ml, from about 1 μg/ml to about 5 mg/ml, from about 1 μg/ml to about 1 mg/ml, from about 1 to about 500 μg/ml, from about 1 to about 500 μg/ml, from about 1 to about 300 μg/ml, from about 1 to about 200 μg/ml, from about 1 to about 100 μg/ml, from about 1 to about 50 μg/ml, from about 1 to about 30 μg/ml, from about 1 to about 20 μg/ml, from about 5 to about 50 μg/ml, from about 5 to about 30 μg/ml, from about 5 to about 20 μg/ml, or from about 5 to about 10 μg/ml. In some instances, the cytokine drug is GM-CSF, and its concentration in the composition may range from about 100 to about 500 mg/ml.

The concentration of each cytotoxic or cytostatic chemotherapeutic drug may range from about 1 μg/ml to about 100 mg/ml, from about 1 μg/ml to about 50 mg/ml, from about 1 μg/ml to about 30 mg/ml, from about 1 μg/ml to about 20 mg/ml, from about 1 μg/ml to about 10 mg/ml, from about 1 μg/ml to about 5 mg/ml, from about 1 μg/ml to about 1 mg/ml, from about 1 to about 500 μg/ml, from about 1 to about 500 μg/ml, from about 1 to about 300 μg/ml, from about 1 to about 200 μg/ml, from about 1 to about 100 μg/ml, from about 1 to about 50 μg/ml, from about 1 to about 30 μg/ml, from about 1 to about 20 μg/ml, from about 5 to about 50 μg/ml, from about 5 to about 30 μg/ml, from about 5 to about 20 μg/ml, or from about 5 to about 10 μg/ml. In some instances, the cytotoxic or cytostatic chemotherapeutic drug is cyclophosphamide, and its concentration in the composition may range from about 10 to about 500 μg/ml.

In some instances, the therapeutic composition comprises, consists essentially of, or consists of the CTLA-4 inhibitor at a concentration of about 0.5 to 10 mg/ml, the PD-1 inhibitor at a concentration of about 0.5 to 20 mg/ml, and either a cytokine drug at a concentration of approximately 1 to 1000 mg/ml (e.g., 100 to 500 mg/ml) or a cytotoxic or cytostatic chemotherapeutic drug at a concentration of approximately 1 to 1000 µg/ml (e.g., 10 to 500 µg/ml). In some instances, the composition comprises the CTLA-4 inhibitor at a concentration of about 1 to 2 mg/ml, the PD-1 inhibitor at a concentration of about 1 to 10 mg/ml, and either a cytokine drug at a concentration of about 10 to about 500 mg/ml (e.g., about 250 mg/ml) or a cytotoxic or cytostatic chemotherapeutic drug at a concentration of about 10 to about 500 µg/ml (e.g., about 250 µg/ml). For example, the composition can comprise the CTLA-4 inhibitor at a concentration of about 3.3 mg/ml, the PD-1 inhibitor at a concentration of about 6.6 mg/ml, and either a cytokine drug at a concentration of approximately 250 mg/ml or a cytotoxic or cytostatic chemotherapeutic drug at a concentration of approximately 16.6 µg/ml. In some instances, the composition comprises the CTLA-4 inhibitor at a concentration of about 0.5 to 10 mg/ml, the PD-1 inhibitor at a concentration of about 0.5 to 20 mg/ml, and either GM-CSF at a concentration of about 100 to about 500 mg/ml (e.g., about 250 mg/ml) or cyclophosphamide at a concentration of about 10 to about 500 µg/ml (e.g., about 250 µg/ml). In some instances, the composition is of a volume of at least or approximately 15 ml. In some instances, the composition is of a volume of at least or approximately 10 ml. In some instances, the composition is of a volume of less than approximately 1.0 ml.

The combination of at least two checkpoint inhibitors and a cytokine drug or cytotoxic or cytostatic chemotherapeutic drug is superior to a combination of at least two checkpoint inhibitors (but without a cytokine drug or cytotoxic or cytostatic chemotherapeutic drug) due to the additive or synergistic effect on the ability of these immune-stimulating drugs to deplete intra-tumoral regulatory T Cells (Tregs). Additionally, generation of an efficient systemic adaptive anti-cancer immune response can be achieved by soft tissue (e.g., intradermal, intramuscular, etc.) immunization strategies that combine Treg depletion with immunogenic tumor cell death and activation of dendritic cells. Traditionally, checkpoint inhibitors are administered intravenously, which can result in serious and sometimes fatal systemic toxicities as a result of non-specific distribution of these cytocidal agents in the body. The non-specific distribution of these agents kills both cancer cells and normal cells and can negatively impact the treatment regimen and patient outcome. Soft tissue injection methods can reduce systemic toxicity and produce fewer side effects by sequestering the drugs in the soft tissue microenvironment and sparing normal cells and tissues from the toxicity of the drugs (see Marabelle et al., "Intratumoral Immunization: A New Paradigm for Cancer Therapy" Clin. *Cancer Res.* 20(7): 1747-56 (2014), which is incorporated herein by reference in its entirety).

Multiple costimulatory and cohibitory receptors influence control T-cell activation, proliferation, and gain or loss of effector function, including CTLA-4. CTLA4 binds B7-1 and B7-2 ligands, promoting anti-cancer activity by activating CD8+ cytotoxic T cells and concomitantly depleting CD4+ Tregs. See Selby et al., "Anti-CTLA-4 antibodies of IgG2a isotype enhance antitumor activity through reduction of intratumoral regulatory T cells" *Cancer Immunol Res* 1:32-42; 2013, which is incorporated herein by reference in its entirety. These results may explain the systemic anti-cancer immune response generated in mouse models with local low dose delivery of anti-CTLA-4. Low doses of anti-CTLA-4 antibody injected around an established mouse colon carcinoma were able to eradicate the local tumor and prevent development of cancer at a distant non-injected site (abscopal effect) by direct enhancement of cancer-specific CD8+ T-cell responses. See Fransen et al., "Controlled local deliver of CTLA-4 blocking antibody induces CD8+ T-cell-dependent tumor eradication and decreases risk of toxic side effects" *Clin Cancer Res* 19: 5381-9; 2013, which is incorporated herein by reference in its entirety.

Moreover, by combining techniques that target both the cancer cells and the immune system, the therapeutic composition can be more effective at not only inhibiting the cancer but also triggering an effective antitumor immune response. This antitumor immune response may then target metastatic sites and eliminate cancer throughout the subject.

The therapeutic composition further comprises a cancer vaccine prepared from tumor or cancer cells, or derivatives thereof, that has been prepared through an ex vivo treatment that kills cancer cells (e.g., creates necrotic and/or necroptotic cancer cells) while minimizing destruction of cancer antigens.

Cancer vaccines typically are vaccines that induce an immune response specific to a type of cancer to treat or prevent the development of that cancer. They may be categorized into tumor-associated antigen-based (TAA) vaccines and dendritic-cell-based (DC) vaccines. Tumor-associated antigen-based vaccines contain a tumor-specific antigen for activation of immune cells. Dendritic-cell-based vaccines are aimed at promoting antigen presentation by dendritic cells to induce antitumor responses. Non-limiting examples of cancer vaccines include tumor cell vaccines, antigen vaccines, dendritic cell vaccines, DNA vaccines, and vector based vaccines.

Cancer vaccines prime the cellular immune response by providing tumor-associated antigens (TAAs) or antigenic epitopes. There are a variety of vaccine delivery platforms, including WIC-specific synthetic or cancer-purified peptides, whole or partial proteins, RNA and DNA plasmids, recombinant viral and bacterial vectors, direct targeting or ex vivo pulsing of dendritic cells, and injection of cancer-derived whole cell lysates, fragments, apoptotic bodies, or exosomes. See Patel et al., "Next generation approaches for tumor vaccination." *Chin Clin Oncol* 6:19 (2017); Gonzalez et al., "Tumor cell lysates as immunogenic sources for cancer vaccine design. *Hum Vaccin Immunother* 10:3261 (2014), which are incorporated by reference in their entirety. Many have limitations that hinder their clinical utility. For example, eradication of cancer and prevention of relapse requires targeting a broad spectrum of TAAs, a major drawback for strategies that employ pre-selected peptides or proteins, plasmids, or recombinant vectors. Dendritic cell vaccination requires ex vivo generation of clinical grade dendritic cells and subsequent loading with cancer-associated antigens or whole cancer cells, a costly, lengthy, and laborious process that has hindered widespread clinical applications of this approach.

The antigens comprise the immune target of the cancer vaccine. To control cancer, vaccines stimulate the host immune system to eradicate (or arrest) large deposits of clinically significant cancer. The antigenic materials introduced into the human subject may take the form of "naked" proteins or peptides with or without adjuvant, proteins expressed by viral vectors and introduced as viral particles, whole cancer cells or lysates expressing a wide range of possible antigens, or recombinant or autologous protein loaded into antigen-presenting cells such as dendritic cells.

Accordingly, the cancer vaccine may be created using whole cancer cells, cell fragments, tissue fragments, lysates, subcellular derivatives such as apoptotic blebs or exosomes, or combinations thereof; which may be fresh, irradiated, fixed (e.g., formalin-fixed, ethanol-fixed, or glutaraldehyde-fixed), and manipulated to create lysates.

Necrotic tumor cells have been shown to induce partial maturation in DC without the need for adjuvants, likely owing to an abundance of heat shock proteins (HSP) 70 and 90 released from dead cells after treatment (see Sauter et al., "Consequences of cell death: exposure to necrotic tumor cells, but not primary tissue cells or apoptotic cells, induces the maturation of immunostimulatory dendritic cells," *J Exp Med.* 191(3):423-34 (2000); Somersan et al, "Primary tumor tissue lysates are enriched in heat shock proteins and induce the maturation of human dendritic cells," *J Immunol.* 167 (9):4844-52 (2001); which are incorporated herein by reference in their entirety). These HSP are recognized by toll-like receptor 4 (TLR4) expressed on DCs, enabling intracellular antigen processing and presentation (see Asea et al. "HSP70 stimulates cytokine production through a CD14-dependent pathway, demonstrating its dual role as a chaperone and cytokine," *Nat Med.* 6(4):435-42 (2000), which is incorporated herein by reference in its entirety). Pro-inflammatory factor high mobility group box 1 (HMGB1) is also released during necrotic cell death, interacts with TLR4 on DCs, and stimulates the processing and presentation of antigens (see Scaffidi et al., "Release of chromatin protein HMGB1 by necrotic cells triggers inflammation," *Nature* 418(6894):191-95 (2002); Apetoh et al., "Molecular interactions between dying tumor cells and the innate immune system determine the efficacy of conventional anticancer therapies," *Cancer Res.* 68(11):4026-30 (2008); which are incorporated herein by reference in their entirety). HMGB1 blocks the fusion of phagosomes with lysosomes by ligating TLR4, thus preventing degradation of antigens and assisting with their trafficking to antigen-presenting cells. Neutralization or knockdown of HMGB1 or knockout of TLR4 abolishes the capacity of dying tumor cells to elicit anti-tumor responses both in vitro and in vivo. Uric acid, an endogenous danger signal, accumulates following purine degradation in injured or dying cells, and also induces DC maturation, thereby enhancing vaccination (see Shi et al., "Molecular identification of a danger signal that alerts the immune system to dying cells," Nature 425(6957): 516-21 (2003), which is incorporated herein by reference in its entirety).

Necroptosis, one of multiple mechanisms of programmed cell death, is characterized by rapid membrane permeabilization via mixed-lineage kinase-like protein (MLKL) and activation of the RIPK1/RIPK3 necrosome complex pathway. Unlike apoptosis, necroptosis robustly stimulates an immune response owing to the release of intracellular contents such as danger-associated membrane proteins (DAMPs), production of inflammatory chemokines and cytokines, and RIPK3 promotion of antigen loading by APCs. Intra-tumoral injection of necroptotic cells in mice can result in CD8+ leukocyte-dependent antitumor immunity.

In one embodiment, the tumor or cancer cells, or derivatives thereof, are fresh whole cells.

The tumor or cancer cells, or derivatives thereof, may be treated ex vivo when preparing a cancer vaccine. The treatments or manipulations include but not limited to: removal of non-cancer tissue by physical or chemical methods to ensure maximized purity of cancer; manipulation or cell alteration (e.g., irradiation, cryosurgical freezing, hyperthermia, radiofrequency manipulation, etc.) to release and expose tumor-associated antigens by mechanisms of apoptosis, necroptosis, or necrosis, and ensuring that the injected vaccine does not contain viable cancer cells; and/or gene transfection (only in fresh samples) to enable production of favorable agents such as cytokines (e.g., GM-CSF).

In one embodiment, the tumor or cancer cells, or derivatives thereof, are cancer cell lysates prepared by one or more treatments such as dissociation or dissection, fixation, centrifugation, resuspension, enrichment, other manipulation, and combinations thereof.

Cancer vaccines can be made from actual cancer cells that have been removed from a subject. Once removed, the cancer cells can be modified in the lab, e.g., by ex vivo treatment to create necrotic and necroptotic cancer cells, so they cannot form more tumors. For example, the cancer cells can be modified by adding chemicals or new genes, to make the cells more likely to be seen as foreign by the immune system. The ex vivo treated cells are then injected into the subject. The immune system is able to recognize the antigens on these cells and through natural physiological processes seeks out and attacks/kills cells that express the intended antigen.

Biopsies or aspiration samples removed from a subject are typically dissected and enriched to ensure a high yield of cancer cells, which are then rendered necroptotic or necrotic. This method generates cell material that contains a crude mixture of cellular fragments of destroyed membranes, intracellular organelles such as mitochondria, and cellular RNA and DNA.

In one embodiment, the tumor or cancer cells, or derivatives thereof, are cancer cell lysates that have been fixed by, for example, formalin, ethanol, or glutaraldehyde. More fixation methods may be found in Wang, et al., "Protective antitumor immunity induced by tumor cell lysates conjugated with diphtheria toxin and adjuvant epitope in mouse breast tumor models" *Chin J Cancer* 31:295-305 (2012); Baogang et al., "Fixed-tumor vaccine: A practical formulation with cytokine-microspheres for protective and therapeutic antitumor immunity" *Chinese-German Journal of Clinical Oncology* 2:196-202 (2003), which are incorporated by reference herein in its entirety.

In one embodiment, the cancer vaccine uses whole cancer cells or lysates. The use of whole cancer cells or lysates offers multiple advantages including: (1) furnishing and targeting all potential tumor-associated antigens; (2) avoiding antigen loss; (3) eliminating the need for prior identification of preferred antigens; (4) targeting all subjects eligible for treatment regardless of HLA type; (5) improving immunogenicity, including higher likelihood of generating MHC-dependent immune stimulation, as antigenic epitopes expressed within cells and/or on the cell membrane induce greater immunogenicity than the same peptides in soluble unbound form; (6) ensuring inclusion of antigens from histologically-identical tumor containing antigenically diverse cells; and (7) providing an abundance of antigens and biomolecules, including proteins, lipids and glycoproteins, that may simultaneously engage and activate numerous types of scavengers receptors such as LOX-1, CD36, and MARCO, and possibly Toll-like receptors on immune cells. See Chiang et al., "Whole Tumor Antigen Vaccines: Where Are We? *Vaccines*" (*Basel*) 3:344 (2015); Seledtsov et al., "Clinically feasible approaches to potentiating cancer cell-based immunotherapies." *Hum Vaccin Immunother* 11:851 (2015), which are incorporated by reference in their entirety.

The cancer vaccine can be autologous or allogenic.

In one embodiment, the cancer vaccine is allogenic, i.e., the tumor or cancer cells, or derivatives thereof, are created from materials derived from another member of the same species to the patient. In other words, cancer cells are taken from a subject, modified, and then injected back into a second, different subject. Commonly used allogeneic materials include use of established laboratory-grown cancer cell lines known to express TAAs of a specific tumor type.

In one embodiment, the cancer vaccine is autologous, i.e., the tumor or cancer cells, or derivatives thereof, are created from materials derived from a patient's tumor or cancer. In other words, cancer cells are taken from a subject, modified, and then injected back into the same subject.

Autologous vaccines may offer superior survival when compared with allogenic vaccines (see Dillman et al., "Randomized phase II trial of autologous dendritic cell vaccines versus autologous tumor cell vaccines in metastatic melanoma: 5-year follow up and additional analyses." *J Immunother Cancer* 6:19 (2014), which is incorporated herein by reference in its entirety). Use of autologous cells can effectively deliver a multivalent patient-specific vaccine treatment that contains large number of antigenic epitopes for priming CD4+ and CD8+ T-cell responses, thereby creating a personal cancer vaccine. For instance, clinical trials of ovarian cancer have successfully utilized whole cancer lysate as a source of antigens for loading dendritic cells, where the vaccines have been shown to be safe and feasible, generating both cellular and humoral immune responses. Other trials in human melanoma, glioma, renal cell carcinoma, prostate cancer, and pancreatic cancer have employed irradiated and/or cryomanipulated allogeneic or autologous tumor cells in combination with the adjuvant proteins, resulting in moderate responses without significant toxicity. See Furukawa et al., "A practical approach to pancreatic cancer immunotherapy using resected tumor lysate vaccines processed to express alpha-gal epitopes" *PLoS One* 12: e0184901 (2017); Plautz et al., "T cell adoptive immunotherapy of newly diagnosed gliomas" *Clin Cancer Res* 6:2209-2218 (2000); Mehrotra et al., "Vaccination with poly(IC:LC) and peptide-pulsed autologous dendritic cells in patients with pancreatic cancer" *J Hematol Oncol* 10:82 (2017); Simons et al., "Induction of immunity to prostate cancer antigens: results of a clinical trial of vaccination with irradiated autologous prostate tumor cells engineered to secrete granulocyte-macrophage colony-stimulating factor using ex vivo gene transfer" *Cancer Res* 59:5160-68 (1999); Jocham et al., "Adjuvant autologous renal tumour cell vaccine and risk of tumour progression in patients with renal-cell carcinoma after radical nephrectomy: phase III, randomised controlled trial. *Lancet* 363:594-99 (2004); all of which are incorporated by reference herein in their entirety.

Autologous vaccine generated from advanced non-small-cell lung cancer cells harvested from pleural effusions can be administered intradermally, generating specific antibody responses against TAAs without significant immune toxicities (see Sanborn et al., "A pilot study of an autologous tumor-derived autophagosome vaccine with docetaxel in patients with stage IV non-small cell lung cancer" *J Immunother Cancer* 5:103 (2017), which is incorporated by reference herein in its entirety). Autologous intradermal cancer vaccine for Ewings sarcoma can provide survival benefit with low and tolerable adverse event level (no>grade 3 toxicity) (see Ghisoli et al., "Three-year Follow up of GMCSF/bi-shRNA (furin) DNA-transfected Autologous Tumor Immunotherapy (Vigil) in Metastatic Advanced Ewing's Sarcoma" *Mol Ther* 24:1478-83 (2016), which is incorporated by reference herein in its entirety).

In one embodiment, the cancer vaccine is autologous and prepared by fixation, such as formalin fixation.

Autologous formalin-fixed tumor vaccine (AFTV) is custom-made from the patient's own surgically extirpated paraffin-embedded cancer tissue and injected intradermally, providing a convenient source of personalized tumor-associated antigens. See Ishikawa et al., "Prospect of Immunotherapy for Glioblastoma: Tumor Vaccine, Immune Checkpoint Inhibitors and Combination Therapy" *Neurol Med Chir* (Tokyo) 57: 321-330; 2017, which is incorporated by reference herein in its entirety.

Formalin fixation preserves the antigenicity of cancer cells, allowing stored surgical tissue to be used to generate an anti-tumor immune response. Cancer-specific autologous cytotoxic T cells can be generated by injection of formalin-fixed sections, with comparable activity and specificity to those induced by cultured cells. See Liu et al., "Induction of human autologous cytotoxic T lymphocytes on formalin-fixed and paraffin-embedded tumour sections" *Nat Med* 1995; 1: 267-271, 1995, which is incorporated by reference herein in its entirety.

AFTV differs from vaccines generated from pre-determined molecule-targeted agents such as peptides in that the autologous cancer serves as a source of a wide array of unidentified patient-specific antigens. Thus, cytotoxic T-cells and dendritic cells induced with AFTV are polyclonal by nature, resulting in a specific cellular immune response against TAAs (tumor associated antigens) (e.g., glypican-3, the protein frequently expressed in hepatocellular carcinoma. See Kawashima et al., "Suppression of post-surgical recurrence of hepatocellular carcinoma treated with autologous formalin-fixed tumor vaccine, with special reference to glypican-3" *Clin Case Rep* 3: 444-447, 2015, which is incorporated herein by reference in its entirety.

AFTV can increase the number of white blood cells and lymphocytes, CD3+ T cells, percentage of Th1 in CD4+ T cells, and ratio of Th1 and regulatory T cells. See Kuranishi et al., "Rate of Clinical Complete Response for 1 Year or More in Bone-Metastatic Breast Cancer after Comprehensive Treatments including Autologous Formalin-Fixed Tumor Vaccine" *Int J Breast Cancer* 4879406, 2018, which is incorporated herein by reference in its entirety. AFTV is also easier and less expensive to prepare and handle than other vaccines, facilitating outpatient office-based treatment. The efficacy of AFTV has been demonstrated pre-clinically in rodent brain tumors and murine liver cancer, and confirmed clinically in patients with breast cancer, glioblastoma multiforme, hepatocellular carcinoma, malignant fibrous histiocytoma, recurrent peritoneal serous carcinoma, cervical small cell carcinoma, upper tract urothelial carcinoma, cholangiocarcinoma, and colon cancer.

However, AFTV immunotherapy has been limited in cases in which the tissue source such as a biopsy contains a small amount of cancer tissue. Also, modification is needed when there is heterogeneous cancer or a mixture of abundant benign cells to ensure a minimum quantity of cancer antigen is included in each vaccine.

In some embodiments of the invention, when the cancer vaccine uses autologous formalin-fixed tumor vaccine, the AFTV source should comprise mostly, if not only, malignant cells and be as representative of the entire targeted cancer as possible.

Other adjuvants or modalities are often added to cancer vaccines to enhance antigen recognition and T cell activation, including 1) genetic or chemical modification of cell-based vaccines; 2) cross-priming tumor-associated antigens to T cells by engaging dendritic cells; 3) T-cell adoptive therapy; 4) stimulation of cytotoxic inflammation by non-specific immunomodulators, toll-like receptor agonists, cytokines, chemokines or hormones; 5) reduction of immunosuppression and/or stimulation of antitumor effector cells using antibodies, small molecules; and 6) various cytostatic or cytoreductive modalities, including chemotherapy. See Patel et al., "Next generation approaches for tumor vaccination." *Chin Clin Oncol* 6:19 (2017), which is incorporated by reference in its entirety. Combining vaccines with immunomodulators improves results, but their full clinical potential has not been reached, likely due to the difficulty in mounting a significant anti-cancer response in subjects because of pre-existing tolerance mechanisms that actively turn off immune recognition and/or disable effector T-cells in the tumor microenvironment. See Chiang et al., "Whole Tumor Antigen Vaccines: Where Are We? Vaccines" (*Basel*) 3:344 (2015); Seledtsov et al., "Clinically feasible approaches to potentiating cancer cell-based immunotherapies." *Hum Vaccin Immunother* 11:851 (2015); Godoy-Calderon et al., "Autologous tumor cells/*Bacillus* Calmette-Guerin/formalin-based novel breast cancer vaccine induces an immune antitumor response" *Oncotarget* 9: 20222-38 (2018), all of which are incorporated by reference in their entirety.

In some embodiments, the cancer lysate may be created from the original starting tissue and comprises whole cells or derivatives thereof, from about 1 million to about 1 billion cancer cells. The lysate may be delivered in a cumulative volume of between about 0.1 to about 10 ml, or from about 0.25 to about 5 ml. The lysate may be delivered to more than one site at the same time.

In some instances, the ex vivo treatment for preparing the tumor or cancer cells or derivative thereof comprises, consists essentially of, or consists of one or more steps of ex vivo radiations and/or manipulations.

The term "manipulation" or "manipulating" as used herein refers to a minimally invasive surgical method to injure or destroy cells, and can be interchangeable with the term "ablation" or "ablating."

The term "cryosurgical freezing" as used herein refers to a process that uses freezing temperature to destroy cancer cells or tissues, and can be interchangeable with the term "cryoablation" or "cryoablating."

The ex vivo radiations and/or manipulations can be performed by using various radiations and/or manipulation methods or combinations thereof known in the art.

Suitable manipulation methods include cold manipulation, such as cryosurgical freezing; thermal manipulation, such as radio frequency (RF) manipulation, microwave manipulation, laser, photo, or plasma manipulation, ultrasonic manipulation, high-intensity focused ultrasound (HIFU) manipulation, or steam manipulation; electrical manipulation, such as reversible electroporation (RE), irreversible electroporation (IRE), radiofrequency electrical membrane breakdown (RF-EMB), RF-EMB type manipulation, manipulation with ultra-short electrical pulse; manipulation using photodynamic therapy; mechanical or physical manipulation such as manipulation using non-thermal shock waves, cavitation, or other mechanical physical means to create cell disruption; chemical manipulation, such as manipulation by injection of chemicals, e.g., alcohol, hypertonic saline, acetic acid, etc.; manipulation with biologics, such as oncolytic viruses; or any combination thereof.

Suitable irradiation or radiation methods include but are not limited to laser radiation (e.g., ultraviolet or near infrared laser radiation), X-ray radiation, or gamma radiation. Suitable radiation includes both solids and liquids. For instance, the radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of 1-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Combining the pharmaceutical composition containing at least two checkpoint inhibitors and a cytokine drug or cytotoxic or cytostatic chemotherapeutic drug with the ex vivo treated (e.g., manipulated) cancer vaccine composition method can provide a systemic, durable, and reproducible cancer immunity. Manipulative techniques, such as cryotherapy and radiation therapy, when used in isolation, produce regulatory T cell inhibition, effector T and B cell activation, and cancer-associated antigen release (see Maia et al., "A comprehensive review of immunotherapies in prostate cancer." *Crit Rev Oncol Hematol.* 113:292-303 (2017), which is incorporated herein by reference in its entirety), effectively creating an adjuvant effect that stimulates the cytotoxic T lymphocyte response. For example, cells rendered necrotic by freeze-thawing have immunostimulatory activity when injected in vivo as they enhance T cell responses to co-injected antigens. See Shi et al., "Cell injury releases endogenous adjuvants that stimulate cytotoxic T cell responses." *Proc Natl Acad Sci USA.* 97(26): 14590-14595 (2000), which is incorporated herein by reference in its entirety.

Injection of the combination of immunotherapeutic drugs and ex vivo manipulated cancer composition can enhance the immune response, perhaps by exploiting the benefits of different mechanisms of action.

Ex vivo manipulation described herein influences at least two factors that are known to influence the immunologic response to a manipulated tumor. One is the effect of the manipulation process on the protein structure and therefore the antigenicity of the tumor proteins. The second factor is the mechanism of cell death related to the manipulation modality.

Necrosis (immediate cell death), under certain conditions, ruptures the cell membrane and causes cell membrane fragments and a wide range of intracellular contents to spill out of the devitalized cells into the extracellular environment that causes co-stimulation of dendritic cells, leading to T Cell proliferation and activation. In contrast, apoptosis (programmed cell death), another form of irreversible injury, in which cells shrivel up and die over time, usually within a few days. Apoptosis leaves the cells intact, confines the cellular contents, and prevents co-stimulation. This lack of intracellular exposure and co-stimulation mutes the immunologic effect by preventing T cell activation and proliferation. Therefore, necrosis greatly elicits immunogenic stimulation, whereas apoptosis usually elicits little or no immune response.

Ex vivo manipulation of cancer cells and subsequent administration into soft tissues induces the body's defense and healing mechanisms to remove it. This creates an opportunity to harness the body's immune defense mechanisms to recognize the dead tumor and essentially auto-immunize the patient against potential cancer neo-antigens (i.e., against the patient's own cancer) (see Veenstra et al., "In situ immunization via non-surgical manipulation to prevent local and distant tumor recurrence" *Oncoimmunology* 4(3): e989762 (2015), which is incorporated herein by reference in its entirety). Moreover, by stimulating the immune system to the cancer cell antigens, the therapeutic approach disclosed herein can (i) treat primary tumors; (ii) activate the immune response to cancer cell antigens; and (iii) induce immune system targeting of metastatic lesions.

Different types of manipulation methods can have different outcomes on the protein structures and mechanism of cell death. For example, heat manipulation destroys structures due to denaturing proteins and it also destroys the underlying collagen matrix of the tissue. This disruption of the proteins and tissue makes a robust immunologic response unlikely. Cold manipulation, e.g. cryosurgical freezing, can denature proteins and can disrupt both protein and tissue structure. Irreversible electroporation (IRE) and non-thermal manipulation modalities, e.g., RF-EMB, are structure sparing and can therefore be used to treat cancers in the pancreas, central liver, and other areas such as the head and neck. IRE is a technique where an electrical field is applied to cells to increase the permeability of the cell membrane. The high voltage of IRE destroys the target cells while leaving neighboring cells unaffected. Radiofrequency electrical membrane breakdown (RF-EMB) is another non-thermal modality that produces necrosis by complete breakdown of the cell membrane electrically (see WO 2015/085162, which is incorporated herein by reference in its entirety). Under certain conditions, RF-EMB can also be used to deliver DNA plasmids. Reversible electroporation (RE) can also be used to deliver DNA plasmids. RE is similar to IRE, however the electricity applied to the target cells is below the electric field threshold of the target cells. Therefore, the cells can recover when the electric field is removed and rebuild their cellular membranes and continue with cellular functions. RE can be used as a tool for gene therapy as the reversible element allows for entry of nucleic acids (e.g. DNA plasmids) into a viable cell. Exemplary ex vivo manipulation treatment methods and brief descriptions of their mechanism are summarized in Table 1.

TABLE 1

Exemplary Manipulation Methods.

| METHOD | MECHANISM | DESCRIPTION |
| --- | --- | --- |
| Thermal | | |
| Microwave | Heat and mechanical | Creates coagulation necrosis with friction and heat |
| HIFU | Heat | Creates necrosis by focusing energy into a small area creating heat |
| Laser | Heat | Creates necrosis with light energy |
| RF Thermal | Heat and mechanical | Creates cellular desiccation and protein coagulation |
| Steam | Heat | Creates coagulation necrosis with heat |
| Cryosurgery | Cold | Creates necrosis by dehydration and ice formation |
| Non-Thermal | | |
| Alcohol, Hypertonic Saline, Acetic Acid Injections | Chemical | Creates coagulative necrosis via dehydration and protein coagulation |
| Photodynamic | Chemical | Creates cell damage by reactive oxygen species and destroying vessels |
| IRE and N-TIRE (Nanoknife) | Electrical | Creates apoptosis with preservation of vessels; delayed necrosis |

For ex vivo treatment of cancer cells to create cancer vaccines, any manipulation method described herein can be used alone or in combination with one or more other manipulation methods. Two or more manipulation methods may be applied sequentially or concurrently. In some cases, a combination of manipulation methods may have a synergistic effect on the tissue. A non-limiting list of combinations includes, for example, heat manipulation and RF-EMB, cryosurgical freezing and RF-EMB, IRE and RF-EMB, RE and RF-EMB, IRE and cryosurgical freezing, heat manipulation and cryosurgical freezing, heat manipulation and IRE, RE and IRE, heat manipulation with RE, and any combination in which two or more methods are used.

In some cases, the ex vivo manipulation methods described herein create an RF-EMB type lesion using a combination of RF-EMB and cryosurgical freezing techniques. This combination of manipulation methods can produce a synergistic effect on the tissue. The synergistic effect can be the creation of an RF-EMB type lesion with less required energy input than with other means. The result, for instance in liver tissue includes: in areas adjacent to aseptic non-inflammatory coagulative necrosis, there is alteration of liver architecture, including dilation of bile duct canaliculi, as well as unique diffuse alteration of cytoplasmic organelles, including distortion of mitochondrial cristae and vacuolization of endoplasmic reticulum.

One of skill in the art would appreciate that the manipulation method described herein can be adapted according to ex vivo applications and the individual aspects of the cancer, e.g., size of the cancer specimen, amount of non-cancer tissue admixed, etc. One of skill in the art would appreciate that the variables of each of the various manipulation methods are known and described in the art (including, for example, Percutaneous Prostate Cryoablation (Edited by Onik, Rubinsky, Watson, and Ablin. Quality Medical Publishing, St Louis, MO, 1995), which is incorporated herein by reference in its entirety).

As examples of the variability and variety of manipulation parameters, the process of cryosurgical freezing includes adjustable variables such as the number of freeze-thaw cycles, the speed of the freeze, the thaw portion of the cycle, to influence the outcome of the manipulation, e.g., the size of the cancer specimen and the immune response to the lesion. Similarly, the process of RF-EMB includes adjustable variables such as the strength of the electric field, frequency, polarity, shape duration, number and spacing, etc., which can similarly influence the outcome of the manipulation. The proximity of a tumor cell to the electric pulse will determine the strength and outcome of the RF-EMB on any particular cell. For example, as the electric field strength diminishes from the point of administration (e.g., the probe), the cells furthest from the point of administration are treated with a lower strength electric field and as such may not be manipulated but rather reversibly electroporated.

In some instances, a first portion or all of a tumor cells or derivatives thereof is manipulated/irradiated ex vivo using a first manipulation/irradiation method and a second portion or all of the tumor cells or derivatives thereof is manipulated/irradiated ex vivo using a second manipulation/irradiation method. The first and the second manipulation/irradiation methods can be the same or different. The first and the second portions of the tumor or cancer cells or derivatives thereof can be the same or different portions of the tumor or cancer cells or derivatives thereof.

In some embodiments, the ex vivo manipulation is performed using both RF-EMB and cryosurgical freezing.

In some instances, the ex vivo manipulating/irradiating step is, at least in part, performed using cryosurgical freezing. As discussed above, cryosurgical freezing is a process that uses cold to destroy tissue and creates necrosis by dehydration and ice formation. Cryosurgical freezing creates necroptotic and necrotic cancer cell death, releasing the full complement of tumor associated antigens (TAAs) necessary for induction of antitumor immunity. The "cryoimmunologic effect," however, is variable.

Cryosurgical freezing used herein differs significantly from conventional cryosurgical freezing: typical cryosurgery is used for complete and immediate destruction of cancer (coagulative necrosis) and creation of negative surgical margins, whereas cryosurgical freezing herein is used to ensure presentation of intact cancer antigens to the immune system to induce an abscopal effect (both necroptosis and necrosis). Moreover, one purpose of the invention is to harness one of the three mechanisms of cell death of cryosurgical freezing (rupture of cell and nuclear membranes and cytoplasmic organelles) and minimize the other two mechanisms (denaturation of proteins and destruction of local microvasculature). This may be accomplished by setting the freezing temperature at $-40°$ C. (temperature-limited) and using ex vivo cryosurgical freezing of fresh cancerous tissues or cells. This combinational therapy may reduce the systemic toxicities associated with traditional systemic cancer treatment and provide for antigen-specific stimulation of the immune system, leading to a personalized tumor-targeted immune response.

Cryosurgical freezing technique typically involves inserting a hollow needle (cryoprobe) into a tissue and then supplying a cryogen to the tip of the cryoprobe. The cryosurgical freezing can be performed using more than one cryoprobe. The cryosurgical freezing can also be performed using any of the multi-purpose probes described herein.

The tissue temperature is decreased to a temperature that correlates with the complete coagulation necrosis. Common cryosurgical freezing techniques involve the use of high pressure (e.g., about 80 psi) liquid nitrogen systems or high pressure (e.g., 3000-4500 psi) argon gas systems. Usually, the freezing of the tissue is subsequently followed by its thawing (usually using a helium gas or resistive heating), which leads to the disruption of cell membranes and induces cell destruction. The cell destruction is further accelerated upon the repetition of the freeze-thaw cycles. In some instances, the ex vivo cryosurgical freezing can comprise, consist essentially of, or consist of at least 1 freeze-thaw cycle. For example, the cryosurgical freezing can comprise between 1 and 4 freeze-thaw cycles. The freeze portion of the freeze-thaw cycle can be, e.g., at least or about 30 seconds long. The freeze portion of the freeze-thaw cycle can range from about 30 seconds to about 15 minutes, from about 30 seconds to about 12 minutes, from about 30 seconds to about 10 minutes, or from 30 seconds to about 5 minutes. The thawing time can be at least or about 30 seconds long. For instance, the thawing time can range from about 30 seconds to about 15 minutes, from about 30 seconds to about 12 minutes, from about 30 seconds to about 10 minutes, or from 30 seconds to about 5 minutes. In some embodiment, the entire cryosurgical freezing step lasts for no more than 30 minutes, no more than 25 minutes, no more than 20 minutes, no more than 15 minutes, no more than 10 minutes, no more than 5 minutes, or no more than 1 minute.

As discussed above, one benefit of the therapeutic composition and treatment method provided herein is inducing immune-stimulating necrosis by ex vivo manipulation. In some embodiments, an ex vivo manipulation is carried out by insertion of a single probe (e.g., a cryosurgery needle probe); the manipulating treatment step lasts for no more than 5 minutes to achieve the desired temperature and effect.

The freeze portion of the freeze-thaw cycle can be performed, e.g., at a temperature between about $-30°$ C. and about $-196°$ C., for instance, from about $-30$ to about $-80°$ C., from about $-35$ to about $-45°$ C., from about $-35$ to about $-40°$ C., from about $-40$ to about $-50°$ C., from about $-40$ to about $-45°$ C., or at about $-40°$ C.

As discussed above, one benefit of the therapeutic composition and treatment method provided herein is preserving cancer neo-antigens by employing minimal thermal manipulation. Cancer neo-antigens are unique foreign proteins present on the internal and external surfaces of cell membranes. These neo-antigens are immunodeterminants and can affect immunotherapy treatment for early cancer recognition and destruction by antigen-specific T-cells. See Desrichard et al., "Cancer neoantigens and applications for immunotherapy" *Clin. Cancer Res.* 22: 807-12 (2016), which is incorporated herein by reference in its entirety. Preservation of neo-antigens is required for immune activation. The immune system is capable of controlling cancer development and mediating regression by generating and activating cancer-neo-antigen-specific dendritic cells and cytotoxic CD8+ T-cells. This allows the immune cells to recognize and target neoantigens on cancer cells at metastatic sites such as lymph nodes and bone.

Most cancer manipulation methods induce necrosis but many fail to preserve the 3-dimensional protein structure of cancer neo-antigens (see Onik et al., "Electrical membrane breakdown (EMB): Preliminary findings of a new method of non-thermal tissue ablation" *J. Clin. Exp. Pathol.* 7:5-11 (2017), which is incorporated herein by reference in its entirety). This can be undesirable as it prevents neo-antigen identification by immune cells.

Accordingly, in some embodiments, ex vivo cryosurgical freezing is employed at relatively low temperatures of about $-40°$ C., rather than the usual $-80°$ C., to preserve the 3-dimensional structure of the neo-antigens. Cryosurgical freezing at about $-40°$ C. creates immune-stimulating necrosis by exceeding the threshold of cell death, while avoiding or minimizing thermal destruction of the protein neo-antigen destruction. See Larson et al., "In vivo interstitial temperature mapping of the human prostate during cryosurgery with correlation to histopathologic outcomes" *Urology* 55:547-52 (2000), which is incorporated herein by reference in its entirety.

In some instances, the ex vivo treatments of the tumor or cancer cells or derivatives thereof further comprise, consist essentially of, or consist of administering a series of electrical pulses. In some instances, the administration of the electrical pulses is performed concurrently with the manipulation. In some instances, the administration of electrical pulses is performed before the manipulation. In some instances, the administration of electrical pulses is performed after the manipulation. The electrical pulses can be administered via the cryoprobe. In some instances, the series of electrical pulses comprise approximately 1 to 1000 pulses and/or comprise a frequency between 100 and 500 kHz. In some instances, the series of electrical pulses comprise approximately 1 to 4000 pulses and/or comprise a frequency between 100 and 500 kHz. In some instances, the series of electrical pulses comprise approximately 1 to 4000 pulses. In some cases, the series of electrical pulses comprises a frequency between 100 and 500 kHz. The electrical pulses can be, e.g., bipolar and/or have instant charge reversal.

Ex vivo manipulating of at least a portion of the tumor or cancer cells or derivatives thereof may be performed using RF-EMB, e.g., using a probe. The probe can be any of the probes disclosed herein. In some instances, the probe administers a series of electrical pulses, thereby creating a manipulation. In some instances, the series of electrical pulses comprise approximately 1 to 1000 pulses. In some instances, the series of electrical pulses comprises approximately 1 to 4000 pulses. In some instances, the electrical pulses comprise a frequency between 100 and 500 kHz. The electrical pulses can be bipolar. The electrical pulses can also have an instant charge reversal.

In some instances, certain ex vivo manipulation methods can create an unique tissue necrosis characterized by the destruction of cell membrane, including many thermal manipulations (e.g., cryosurgical freezing) and RF-EMB. Upon destruction of the cellular membrane, the intracellular components and constituent parts of the cell membrane disperse into the extracellular space whereby immunologic identification and response is enhanced. This is different than other types of manipulation methods (for example, IRE) which create tissue apoptosis.

As used herein, the term "RF-EMB type manipulation" refers to any manipulation technique or combination of techniques which, when performed, yields essentially the same results as RF-EMB manipulation.

Such ex vivo manipulation brings at least one of the following benefits: intracellular components and membrane antigens of the cells are not or minimally denatured by the manipulation; the amount of exposed intracellular components and membrane antigens of the cells is sufficient to stimulate the immune system; and/or the amount of exposed intracellular components and membrane antigens of the cells do not or minimally create immune tolerance. In one embodiment, the ex vivo manipulation preserves the structure of cancer neo-antigens such that the antigen stimulates the immune system.

In certain embodiments, the cancer vaccine is prepared by ex vivo treatment comprising one or more of irradiation and manipulation (such as cryosurgical freezing), and is exposed to the at least one drug (a cytokine, a cytotoxic or cytostatic chemotherapeutic drug, or combinations thereof).

In some instances, the cancer vaccine is prepared by ex vivo treatment comprising UV-irradiation and cryosurgical freezing, and is exposed to the at least one cytokine (e.g., GM-CSF) or cytotoxic or cytostatic chemotherapeutic drug (e.g., cyclophosphamide) in low-dose. In one embodiment, the cryosurgical freezing is carried out at a temperature ranging from about −35 to about −100° C., e.g., about −40° C. In one embodiment, the cryosurgical freezing can be carried out using a single probe, with total manipulating time of no more than 10 minutes. In one embodiment, the cancer vaccine is suspended in a low-dose solution of GM-CSF (e.g., at a dosage of 250 mg) or cyclophosphamide (e.g., at a dosage of 200-300 mg/m$^2$).

The therapeutic composition may or may not be administrated to the subject in need in a single administration. Various components of the therapeutic composition can be administered to the subject concurrently or sequentially. For instance, the checkpoint inhibitors, cytokine drug or cytotoxic or cytostatic chemotherapeutic drug, and ex vivo treated cancer vaccine can be administered to the subject concurrently. Alternatively, administration of each of the checkpoint inhibitors can be performed, e.g., prior to, concurrently with, and/or after the administration of each of the cytokine drugs or cytotoxic or cytostatic chemotherapeutic drugs, and/or the ex vivo treated cancer vaccine. Administration of each of the cytokine drugs or cytotoxic or cytostatic chemotherapeutic drugs can be performed, e.g., prior to, concurrently with, and/or after the administration of each of the checkpoint inhibitors, and/or the ex vivo treated cancer vaccine. Administration of the ex vivo treated cancer vaccine can be performed, e.g., prior to, concurrently with, and/or after the administration of each of the checkpoint inhibitors and/or each of the cytokine drugs or cytotoxic or cytostatic chemotherapeutic drugs.

In one embodiment, the cytokine drug (e.g., GM-CSF) or cytotoxic or cytostatic chemotherapeutic drug (e.g., cyclophosphamide) is administered at the time of cancer vaccination. This can be achieved by, e.g., preparing the cancer vaccine in the suspension of the cytokine drug or cytotoxic or cytostatic chemotherapeutic drug.

In one embodiment, the cytokine drug (e.g., GM-CSF) or cytotoxic or cytostatic chemotherapeutic drug (e.g., cyclophosphamide) can be administered (e.g., subcutaneously or orally) following the cancer vaccination.

In one embodiment, the cytokine drug (e.g., GM-CSF) or cytotoxic or cytostatic chemotherapeutic drug (e.g., cyclophosphamide) is administered at the time of cancer vaccination, and an additional administration of a same or different cytokine drug (e.g., subcutaneously) or cytotoxic or cytostatic chemotherapeutic drug (e.g., orally) follows the cancer vaccination.

Regulatory T lymphocyte ($T_{Reg}$) populations are sensitive to sub-clinical doses of the chemotherapy agent cyclophosphamide. At low doses of cyclophosphamide, circulating $T_{Reg}$ in animal models diminish with very little impact on other white cell populations. Sub-cytotoxic doses of cyclophosphamide or GM-CSF have not shown to have resulted in immune enhancement result. Although cyclophosphamide or GM-CSF has been used as an immunopotentiating agent in a number of clinical trials of active-specific immunotherapy (e.g. cancer vaccine) studies of advanced cancer, low dose (typically 250-300 mg/m$^2$) cyclophosphamide or GM-CSF is typically administered 3-4 days prior to the vaccine regimen. Here, administration of cyclophosphamide or GM-CSF at the time of cancer vaccination can facilitate mobilization of T-cells and other immune stimulating cells at the time of vaccination; additional administration following, during, or after vaccine therapy can institute an ongoing but limited regimen following vaccine therapy, to account for any "rebound" of TReg that might defeat an incipient immune response.

In certain embodiments, the cancer vaccine is prepared by ex vivo UV irradiation, exposure to low-dose cyclophosphamide or GM-CSF, and temperature-limited cryosurgical freezing of the cancerous tissue sample, creating a personalized vaccine lysate of necrotic and necroptotic cells and intact tumor-associated antigens that, when being injected (e.g., intra-dermally or intra-tumorally), can prime the immune system to target cancer cells. In one embodiment, following the injection of such cancer vaccine lysate, two immunotherapeutic drugs (e.g., PD-1 inhibitor monoclonal antibody nivolumab (or pembrolizumab) and anti-CTLA-4 monoclonal antibody ipilimumab) are sequentially injected (e.g., intra-dermally or intra-tumorally) immediately, preferably at the same site. Additionally, low-dose GM-CSF may be administered afterwards for a period of time (e.g., 6 weeks) to prolong the immune response; oral low-dose cyclophosphamide may be administered afterwards for a period of time (e.g., 6 weeks) to prolong the immune response.

One exemplary therapeutic composition and treatment methods for treating metastatic solid cancer entails the following three therapeutic components and treatment regime:
  (a) ex vivo treatment of fresh cancer cells from biopsy or needle aspiration by UV irradiation, low-dose cyclophosphamide or GM-CSF, and temperature-limited cryosurgical freezing to:

a. create a personalized vaccine lysate of necrotic and necroptotic cancer cells while minimizing destruction of cancer antigens, thereby ensuring good immune response;
b. provide a full complement of tumor-associated antigens and associated cytokines and other immunostimulants released from the cancer cells, and
c. initiate the process of suppressing inhibitory signals from T-regulatory cells; followed by:
(b) sequential intra-dermal or intra-tumoral injection of cancer lysate vaccine (autologous) and two check point inhibitors with complementary roles that target different pathways to create a synergistic or potentiated anti-cancer effect, for instance:
a. CTLA-4 inhibitor to suppress inhibitory signals from T-regulatory cells and prolong an anti-tumor cytotoxic T-cell response, and
b. PD-1 inhibitor to reverse T-cell exhaustion and strengthen antitumor activity by "unmasking" cancer neoantigens, thereby exposing the cancer cell antigens to dendritic cells and cytotoxic (killer) T-cells while facilitating the cytotoxic T-cell's anti-tumor activity;
followed by:
(c) subsequent administration of low-dose cyclophosphamide (e.g., orally) or GM-CSF (e.g., subcutaneously) to prolong immune cell mobilization.

Without being bound by theory, cancer neoantigens and immunostimulants such as cytokines contained within the cancer lysate vaccine may be available in the dermis at the site of skin injection, a rich source of immature dendritic cells and other immune cells, or intra-tumorally. Resident immature antigen-presenting cell (APCs) (e.g., dendritic cells), T-cells, and other immune cells at the injection site can then internalize neoantigens to become activated to recognize cancer-specific antigenic proteins. The activated dendritic cells can drain into the nearby lymph nodes and activate T-cells that target the cancer-specific neoantigens and recruit other cytotoxic T-lymphocytes to destroy cancer cells throughout the body that harbor the precise antigenic epitopes, thereby stimulating the abscopal (bystander) effect. In this way, dendritic cells are capable of initiating cell-mediated systemic anti-tumor immune response in combination with cytotoxic T-cells. Regulatory T lymphocytes, which have been implicated in dampening or halting cell-mediated antigen-specific immune responses, can be selectively depleted by anti-CTLA-4 monoclonal antibodies and low-dose cyclophosphamide or GM-CSF. Intra-dermal or intra-tumoral injection of drugs induce fewer side effects than systemic therapy.

The therapeutic compositions can further include one or more therapeutically effective amount of therapeutic and/or biologic agents known in the art to be effective in treating cancer, i.e., an anti-cancer agent, or a an agent known in the art to be effective in stimulating the immune system, i.e., immunostimulant or immunomodulator. Such therapeutic compositions can be used to treat cancer as described herein.

The therapeutic composition can also comprise one or more therapeutically effective amount of nucleic acid drugs. The nucleic acid drug can be, e.g., DNA, DNA plasmid, nDNA, mtDNA, gDNA, RNA, siRNA, miRNA, mRNA, piRNA, antisense RNA, snRNA, snoRNA, vRNA, etc. For example, the nucleic acid drug can be a DNA plasmid. In some instances, the DNA plasmid can comprise, consist essentially of, or consist of a nucleotide sequence encoding a gene selected from the group consisting of GM-CSF, IL-12, IL-6, IL-4, IL-12, TNF, IFNy, IFNa, and/or a combination thereof. The nucleic acid drug can have clinical usefulness, for example, in enhancing the therapeutic effects of the cells or providing a patient with a therapeutic agent. In another instance, the nucleic acid drug may function as a marker or resistance gene. The nucleotide sequence can encode a gene that can be secreted from the cells or cannot be secreted from the cells. The nucleic acid drug can encode a gene and a promoter sequence to increase expression of the gene.

The therapeutic composition can also comprise one or more therapeutically effective amount of toll-like receptors (TLR). The toll-like receptor can be selected from the group consisting of TLR1, TLR2, TLR3, TLR4, TLR5, TLR6, TLR7, TLR8, TLR9, TLR10, TLR11, TLR12, TLR13, and/or a combination thereof. In some embodiments, the toll-like receptor can be TLR3. In some embodiments, the therapeutic composition can include a first TLR and a second TLR. In some instances, the first and the second TLR are the same; and in other instances, they are different. The TLR may be delivered at a concentration of about 0.01 to about 5 mg/m$^2$.

One skilled in the art would appreciate that the therapeutic compositions can be adapted according to the individual aspects of the cancer and/or the subject, e.g., the size of the tumor, the location of the tumor, the subject, clinical evidence of drug response, etc.

The therapeutic composition can include a delivery agent or pharmaceutically acceptable carrier or excipient. As used herein the term "pharmaceutically acceptable carrier or excipient" includes solvents, dispersion media, coatings, antibacterial and antifungal agents, isotonic and absorption delaying agents, and the like, compatible with pharmaceutical administration. These carrier or excipient does not destroy the pharmacological activity thereof and is nontoxic when administered in doses sufficient to deliver a therapeutic amount of the composition. Supplementary active compounds can also be incorporated into formulation for the therapeutic composition that contains an antibody or antigen-binding fragment thereof as described herein.

The therapeutic composition can be formulated for various administrative routes, including but not limited to, orally or parenterally, such as intravenously, intramuscularly, subcutaneously, intra-tumorally, intra-orbitally, intra-capsularly, intra-peritoneally, intra-rectally, intra-cisternally, intra-vasally, intra-dermally (e.g., via skin or soft tissue); by passive or facilitated absorption through the skin using, for example, a skin patch or transdermal iontophoresis, respectively; by being administered to the site of a pathologic condition, for example, intravenously or intra-arterially into a blood vessel supplying a tumor; or combinations thereof.

Methods of formulating suitable therapeutic/pharmaceutical compositions are known in the art (see, e.g., Troy, "Remington: The Science and Practice of Pharmacy" (21$^{st}$ Ed., Lippincott Williams & Wilkins, 2006); Willig, "Drugs and the Pharmaceutical Sciences: a Series of Textbooks and Monographs" (M. Dekker, 1975); both of which are hereby incorporated by reference in their entirety. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The pH value can be adjusted with acids or bases, such as hydrochloric acid or sodium hydroxide. The parenteral preparation can be enclosed in ampoules, disposable syringes or multiple dose vials made of glass or plastic.

In some embodiments, the therapeutic compositions and components thereof are formulated for intradermal or subcutaneous administration and can be injected intradermally or subcutaneously. For instance, the components of the therapeutic compositions are formulated for intradermal administration, such as skin or soft tissue administration, and can be injected intradermally, via skin or soft tissue.

The therapeutic composition or various components of the therapeutic composition (e.g., the checkpoint inhibitors, cytokine drugs or cytotoxic or cytostatic chemotherapeutic drugs, cancer vaccines, nucleic acid drugs, and/or a combination thereof) may be formulated for soft tissue delivery. For example, the therapeutic composition or various components of the therapeutic composition can be intra-dermally delivered via an injection device. The injection device may be part of a probe. The probes as described herein can be configured for the various manipulation methods. Further, the probe can also be configured to combine the methods described herein, e.g., a cryoprobe can be configured to administer an electric pulse, a cryogen, a chemical or biological manipulation agent, and/or a composition of drugs.

A combination of at least two checkpoint inhibitors and a cytokine drug or cytotoxic or cytostatic chemotherapeutic drug administered into benign or cancerous soft tissue produces fewer adverse side effects and/or immune-related adverse events than a combination of the two checkpoint inhibitors (without the cytokine drug or cytotoxic or cytostatic chemotherapeutic drug) administered intravenously. The combination of these three or more immune-stimulating drugs delivered into benign or cancerous soft tissue may be sufficient to trigger a systemic CD4+ and CD8+ T-cell mediated anti-tumor immune response which can eradicate distant metastatic tumor sites, including in the central nervous system in mice. This local combination strategy may also generate a better CD8+ memory anti-tumor immune response because it prevents late tumor relapses as opposed to systemic delivery of antibodies.

The skin is a preferred portal for delivery of anti-cancer vaccines, serving as a convenient injection site that obviates the need for and risks created by intravenous injection or surgical intratumoral manipulation and drug manipulation, allowing cancer cell lysates and adjuvants to be safely administered. See Patel et al., "Next generation approaches for tumor vaccination." *Chin Clin Oncol* 6:19 (2017), which is incorporated by reference in its entirety. Intradermal drug injection can reduce systemic toxicity and produce fewer side effects by sequestering the drugs in the skin microenvironment (see Marabelle et al., "Intratumoral Immunization: A New Paradigm for Cancer Therapy" *Clin. Cancer Res.* 20(7): 1747-56 (2014), which is incorporated herein by reference in its entirety). Intradermal injection delivers antigen directly into the skin, an anatomical site that contains a dense and diverse population of immune cells, including antigen-presenting dendritic cells and effector T cells, with greater potential for immunogenicity than intramuscular injection of a given amount of antigen (see Kenney et al., "Dose Sparing with Intradermal Injection of Influenza Vaccine" N Eng J Med 351, 2295-301 (2004); Patel et al., "Next generation approaches for tumor vaccination." *Chin Clin Oncol* 6:19 (2017), which are incorporated by reference in their entirety). For example, bacille Calmette-Guerin vaccine is routinely injected intradermally.

Intradermal administration of cancer lysate products potentiates ingestion by five subsets of lymph-node migratory skin dendritic cells (DCs) (Langerhan's cells, Langerin, CD103−, CD103+, CD11b+, and CD11b−) (see Vardam et al., "Langerhans Cells Orchestrate TFH-Dependent Humoral Immunity" *J Invest Dermatol* 137:1826-1828 (2017), which is incorporated by reference in its entirety). After recruitment and activation, these DCs process the tumor associated antigens (TAAs) into peptides that are bound to major histocompatibility complex 1 (MHC-1) for CD8+ T cells or MHC-II for CD4+ T cells, and then migrate from the skin to draining lymph nodes and cross-present the TAAs to their cognate T cells, stimulating the priming and expansion of effector T-cells and induction of follicular center T cell differentiation. See Ruben et al., "In situ loading of skin dendritic cells with apoptotic bleb-derived antigens for the induction of tumor-directed immunity" Oncoimmunol 3; 7: e946360 (2014), which is incorporated herein by reference herein in its entirety. The immune response in lymph nodes is thus triggered by the combination of antigen recognition (presentation of TAAs in the context of MEW molecules by DCs and T-cell receptors of T lymphocytes) and immune activation (generation of a type 1 helper T-cell response that generates cytotoxic T lymphocytes, as well as type 2 helper T-cell response that results in production of antigen-specific antibodies to induce cell-mediated cell death) (see Dillman et al., "Randomized phase II trial of autologous dendritic cell vaccines versus autologous tumor cell vaccines in metastatic melanoma: 5-year follow up and additional analyses." *J Immunother Cancer* 6:19 (2014), which is incorporated herein by reference in its entirety). The activated antigen-specific T cells then migrate to the site of cancer, likely guided by chemokine gradients and other inflammatory cues, where they recognize tumor cells via interaction between the T-cell receptors on T lymphocytes and antigens in the presence of WIC molecules on cancer cells. The cytotoxic T cells release enzymes such as perforin and granzyme-B, resulting in cell necrosis, and this lytic effect on tumor cells incites a positive feedback loop that results in release of more antigens to begin the "cancer-immunity cycle" again. Release of other antigens also causes an expanded response referred to as "antigen spreading." See Patel et al., "Next generation approaches for tumor vaccination." *Chin Clin Oncol* 6:19 (2017), which is incorporated by reference herein in its entirety.

In combination with dendritic cell activation, intradermal cancer vaccine administration also stimulates many of the 1 million T cells/cm$^2$ resident in normal human skin, including two subsets of long-lived memory CD8C T cells that confer durable protective adaptive and innate immunity against foreign antigens (pathogens, TAAs, etc): (1) resident-memory cells (Trm), standing sentry in numerous non-lymphoid tissues (including skin, gastrointestinal tract, brain, and lung) that constitutively express CD69 and CD103; and (2) effector-memory cells (Tem) that circulate between blood and non-lymphoid tissue and express tissue-homing receptors. A third subset of memory CD8C T cells, central-memory cells (Tcm), circulates between blood and lymphoid tissue, expressing CD62L and CCR7. Upon antigen re-challenge, all of these T cells are activated and proliferate, but the Trm cells are the first and most potent local rampart, secreting an abundance of effector cytokines and chemokines (e.g., IFN-g, granzyme B) that results in targeted engagement of Tcm, Tem, B cells, and other immune cells. The intradermal route of vaccination is able to stimulate production of antigen-specific Trm cells that amass locally and in non-vaccinated skin. See Galvez-Cancino et al., "Vaccination-induced skin-resident memory CD8(+) T cells mediate strong protection against cutaneous melanoma" *Oncoimmunology* 7:e1442163 (2018), which is incorporated by reference herein in its entirety.

Skin injection of immune stimulating drugs can reduce systemic toxicity and produce fewer side effects by preventing their immediate circulation at high concentrations in the blood. This route of delivery also produces much higher concentrations of immunostimulatory products in the microenvironment than with systemic infusion, thereby potentiating better efficacy. On the other hand, this route of delivery also allows for lowering the amount of the administered compositions necessary to be therapeutically effective. For example, dermally-applied cancer lysate vaccines generate potent immunotherapeutic responses that are equivalent or superior to other needle-based vaccinations such as intramuscular injection despite 5-10 fold dose reduction of antigen. See Depelsenaire et al., "Colocalization of cell death with antigen deposition in skin enhances vaccine immunogenicity" *J Invest Dermatol* 134:2361-2370 (2014), which is incorporated by reference herein in its entirety.

Pre-clinical intradermal (ID) delivery of cancer vaccines has proven safe and effective in a large and diverse number of cancers. Chen and colleagues found that mice injected with whole cell cancer lysate vaccine combined with GM-CSF stimulated and activated intradermal DCs, resulting in cancer phagocytosis, presentation of cancer-specific tumor antigens, migration of DCs, and stimulation of other immune cells. See Chen et al., "Leveraging Engineering of Cells for Drug Delivery" *Acc Chem Res* 51:668-77 (2018), which is incorporated by reference herein in its entirety. In a murine model, ID administration of antigen-specific Trm cell-stimulating vaccines resulted in infiltration and suppression of melanoma growth that was independent of circulating CD83 T cells. See Galvez-Cancino et al., "Vaccination-induced skin-resident memory CD8(+) T cells mediate strong protection against cutaneous melanoma" *Oncoimmunology* 7: e1442163 (2018), which is incorporated by reference herein in its entirety. Murine injection of breast cancer cell lysate combined with heat shock protein fragments and diptheria toxin resulted in favorable humoral and cellular immune responses and protective anti-tumor immunity. See Wang, et al., "Protective antitumor immunity induced by tumor cell lysates conjugated with diphtheria toxin and adjuvant epitope in mouse breast tumor models" *Chin J Cancer* 31:295-305 (2012), which is incorporated by reference herein in its entirety. Half of all colon cancers in a murine model were eradicated by ID immunization with cancer vaccine consisting of baculovirus, a CT26 colon cancer lysate, and a cytotoxic T-cell epitope peptide; the antitumor effect correlated with tumor antigen-specific response of CD8C T cells. See Kawahara, et al. "A tumor lysate is an effective vaccine antigen for the stimulation of CD4(+) T-cell function and subsequent induction of antitumor immunity mediated by CD8(+) T cells" *Cancer Biol Ther* 16:1616-25 (2015), which is incorporated by reference herein in its entirety. ID injection in dogs of autologous B-cell lymphoma cell membrane fragments combined with IL-2 and GM-CSF generated specific cell-mediated immunity and delayed-type hypersensitivity reactions with no significant toxicity. See Henson et al., "Immunotherapy with autologous tumour antigen-coated microbeads (large multivalent immunogen), IL-2 and GM-CSF in dogs with spontaneous B-cell lymphoma" *Vet Comp Oncol* 9:95-105 (2011), which is incorporated by reference herein in its entirety. Vaccination with irradiated GM-CSF-producing cancer cells increased survival of mice with tumors implanted in the brain. See Sampson et al., "Immunotherapy for Brain Tumors" *J Clin Oncol* 356:2450-56 (2017), which is incorporated by reference herein in its entirety. Vaccination with irradiated Lewis lung cancer cell line transfected to produce IL-18 and GMCSF created an anti-cancer response that included proliferation of cytotoxic T-cells and prolonged survival in a murine model. See Tian et al., "Cellular immunotherapy using irradiated lung cancer cell vaccine co-expressing GM-CSF and IL-18 can induce significant antitumor effects" *BMC Cancer* 14:48 (2014), which is incorporated by reference herein in its entirety.

Similar to the pre-clinical findings, treatment with ID cancer vaccination in patients has also proven to be safe, well-tolerated, and effective in multiple cancers. Mehrotra et al. intradermally delivered a combination of Poly-ICLC and an autologous DC vaccine pulsed with HLA-A2-restricted peptides hTERT, CEA, and survivin to 8 patients with pancreatic cancer. See Mehrotra et al., "Vaccination with poly(IC:LC) and peptide-pulsed autologous dendritic cells in patients with pancreatic cancer" *J Hematol Oncol* 10:82 (2017), which is incorporated by reference herein in its entirety. Treatment was well-tolerated, with the common symptoms being fatigue and/or self-limiting flu-like symptoms. Four patients experienced stable disease, while four patients had disease progression; median overall survival was 7.7 months. MHC class I-tetramer analysis before and after vaccination revealed effective generation of antigen-specific T cells in three patients with stable disease. Treatment of patients with metastatic cancer of different sites with intradermal injections of dendritic cells loaded with autologous cancer cell lysate was well tolerated, limited to grade 1 and 2 adverse events such as fever, asthenia, and pain at the injection site. See Alfaro et al., "Pilot clinical trial of type 1 dendritic cells loaded with autologous tumor lysates combined with GM-CSF, pegylated IFN, and cyclophosphamide for metastatic cancer patients" *J Immunol* 187:6130-42 (2011), which is incorporated by reference herein in its entirety. Treatment Intradermal polyvalent vaccination with irradiated whole cells from multiple melanoma cell lines in combination with BCG resulted in 26% response over 19 months in high-stage patients with minimal adverse events. See Vilella et al., "Treatment of patients with progressive unresectable metastatic melanoma with a heterologous polyvalent melanoma whole cell vaccine" *Int J Cancer* 106:626-31 (2003), which is incorporated by reference herein in its entirety. Use of an autologous hapten-modified melanoma vaccine resulted in regression of pulmonary metastases. See Berd et al., "Induction of cell-mediated immunity to autologous melanoma cells and regression of metastases after treatment with a melanoma cell vaccine preceded by cyclophosphamide" *Cancer Res* 46: 2572-77 (1986), which is incorporated by reference herein in its entirety. Treatment with a polyvalent vaccine in high-stage melanoma improved survival at 5 years when compared to other treatments when metastases had been completely resected (often to multiple sites) prior to vaccine therapy. See Vilella et al., "Treatment of patients with progressive unresectable metastatic melanoma with a heterologous polyvalent melanoma whole cell vaccine" *Int J Cancer* 106:626-31 (2003), which is incorporated by reference herein in its entirety.

In one embodiment, the therapeutic compositions are formulated for intratumoral administration, and can be injected intratumorally.

Intratumoral injection of immune-stimulatory drugs in humans can significantly lower the adverse event rate of systemic immunotherapy when compared with intravenous injection. Systemic administration of the combination of immunotherapy drugs such as PD1/PD-L1 (e.g., Keytruda, Opdivo) and anti-CTLA-4 (e.g., Yervoy) has a high adverse event rate. Intra-tumoral injection avoids many adverse events and allows combinations of drugs with different mechanisms of action to be employed.

Studies in animal models have shown that local co-stimulation using agonistic antibodies drive systemic anti-tumor effects and induce T-cell-dependent anti-tumor immunological memory with less toxicity than expected from systemic treatment. Injection in or near the tumor assists in generating the systemic tumor effect. For instance, injection in or near the tumor can result in increased accumulation in the tumor-draining lymph nodes and reduced Cmax (maximum serum concentration), as compared to systemic administration.

Therapeutic compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, NJ), or phosphate buffered saline (PBS). It is desirable that the composition be sterile and fluid to the extent that easy syringability exists. The therapeutic composition should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it is desirable to include isotonic agents, for example, sugars, polyalcohols such as mannitol, sorbitol, and sodium chloride in the therapeutic composition. Prolonged absorption of the injectable compositions can be brought about by including in the therapeutic composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the desirable methods of preparation are vacuum drying and freeze-drying, which yield a powder of the active ingredient plus any additional desired ingredient from a previously sterile-filtered solution thereof. In some embodiments, the therapeutic compositions can be prepared with carriers that will protect the active compounds against rapid elimination from the body, such as a controlled release formulation, including implants and microencapsulated delivery systems.

The therapeutic compositions can be included in a container, pack, cartridge, or dispenser together with instructions for administration.

The term "administer" or "administration" in relation to the methods include not only the actions of prescriptions and/or instructions from a medical professional, but also the actions of taking the prescriptions and/or instructions of a patient and the actions of actually taking the composition or treatment steps by the patient.

Another aspect of the invention provides methods of treating a tumor or a cancer in a subject in need. The method can comprise, consist essentially of, or consist of administering to the subject in need a therapeutic composition comprising i) at least two immune checkpoint inhibitors, ii) at least one drug selected from a cytokine, a cytotoxic or cytostatic chemotherapeutic drug, and combinations thereof, and iii) a cancer vaccine prepared from tumor or cancer cells, or derivatives thereof, that have been prepared through an ex vivo treatment that creates necrotic and/or necroptotic cancer cells while minimizing destruction of cancer antigens, each being present in the composition in a therapeutically effective amount to treat the tumor or cancer. The composition can optionally contain a pharmaceutically acceptable carrier. For example, the administered composition may be the therapeutic compositions described herein.

All above embodiments relating to the aspect of the therapeutic composition, including suitable immune checkpoint inhibitors, suitable cytokine drugs or suitable cytotoxic or cytostatic chemotherapeutic drugs, cancer vaccine and its preparation by suitable ex vivo treatment methods, suitable optional pharmaceutically acceptable carriers, their effective amounts for treating tumor or cancer, and the formulations of the therapeutic composition for various administrative routes are applicable in this aspect of the method of treating a tumor or a cancer in a subject.

In some embodiments, the method further comprises creating a cancer vaccine by ex vivo treatment from tumor or cancer cells, or derivatives thereof. The ex vivo treatments of tumor or cancer cells, or derivatives thereof, for preparation of cancer vaccines have been described herein in the aspect of the therapeutic composition and are applicable to this aspect of the method of treating a tumor or a cancer.

In one embodiment, the method further comprises dissociating cells or cellular components from tumor or cancer specimens ex vivo using mechanical, enzymatic, or other methods known to one skilled in the art, and centrifuging and resuspending the cells in a sterile fluid such as buffered saline, prior to further manipulations such as manipulation.

In some instances, the method comprises, consists essentially of, or consists of administering the therapeutic composition to the patient intra-dermally, intra-tumorally. In some instances, the method comprises, consists essentially of, or consists of administering the therapeutic composition to the patient's skin or soft tissues. The administration may be carried out by using an injection device.

In some embodiments, the method comprises, consists essentially of, or consists of administering to the patient a composition comprising i) at least two different immune checkpoint inhibitors, each being an inhibitor of an immune checkpoint molecule selected from the group consisting of CD137, CD134, PD-1, KIR, LAG-3, PD-L1, PDL2, CTLA-4, B7.1, B7.2, B7-DC, B7-H1, B7-H2, B7-H3, B7-H4, B7-H5, B7-H6, B7-H7, BTLA, LIGHT, HVEM, GALS, TIM-3, TIGHT, VISTA, 2B4, CGEN-15049, CHK 1, CHK2, A2aR, TGF-β, PI3Kγ, GITR, ICOS, DO, TLR, IL-2R, IL-10, PVRIG, CCRY, OX-40, CD160, CD20, CD52, CD47, CD73, CD27-CD70, and CD40; ii) at least one cytokine or cytotoxic or cytostatic chemotherapeutic drug, and iii) a cancer vaccine prepared from tumor or cancer cells, or derivatives thereof, that have been prepared through an ex vivo treatment that creates necrotic and/or necroptotic cancer cells while minimizing destruction of cancer antigens, in an amount effective to treat the tumor or cancer. In some embodiments, the at least two checkpoint inhibitors comprises a CTLA-4 inhibitor, a PD-1 inhibitor. In some embodiments, the at least two checkpoint inhibitors comprises a CTLA-4 inhibitor and a PD-L1 inhibitor.

In some embodiments, the method comprises, consists essentially of, or consists of administering to the patient a composition comprising i) at least two immune checkpoint inhibitors; ii) at least one cytokine selected from the group consisting of erythropoietin, G-CSF, GM-CSF, IL-2, IL-4, IL-6, IL-12, TNF, interferons such as INF-α-2a, INF-α-2b, INF-β, INF-γ, and combinations thereof; or at least one cytotoxic or cytostatic chemotherapeutic drug selected from the group consisting of asparaginase, bleomycin, busulphan, carboplatin, cetuximab, cisplatin, cyclophosphamide, BCG, chloramphenicol, colchicine, cyclosporin, dacarbazine, doxorubicin, etoposide, fludarabine, gemcitabine, ifosfamide, irinotecan, lomustin, melphalan, methotrexate, mitomycin, mitoxantrone, paclitaxel, procarbazine, rituximab, temozolomide, thitepa, vinblastine, vincristine, zidovudine, and combinations thereof, and iii) a cancer vaccine prepared from tumor or cancer cells, or derivatives thereof, that have been prepared through an ex vivo treatment that creates necrotic and/or necroptotic cancer cells while minimizing destruction of cancer antigens, in an amount sufficient to treat the tumor or cancer. In one embodiment, the composition comprises at least one cytokine, and at least one of the cytokines is GM-CSF. In one embodiment, the composition comprises at least one cytotoxic or cytostatic chemotherapeutic drug, and at least one of the cytotoxic or cytostatic chemotherapeutic drugs is cyclophosphamide.

As discussed above, the therapeutic composition may or may not be administered to the subject in need in a single administration. The methods of administration of the therapeutic composition and/or various components of the therapeutic composition have been described herein in the aspect of the therapeutic composition and are applicable to this aspect of the method of treating a tumor or a cancer.

In one embodiment, the method comprises administering to the subject the checkpoint inhibitors, cytokine or cytotoxic or cytostatic chemotherapeutic drug, and ex vivo treated cancer vaccine concurrently.

In one embodiment, the method comprises:
 i) administering each of the checkpoint inhibitors,
 ii) prior to, concurrently with, and/or after i), administering each of the cytokine drugs or cytotoxic or cytostatic chemotherapeutic drugs, and
 iii) prior to, concurrently with, and/or after i) or ii), administering the ex vivo treated cancer vaccine.

In one embodiment, the method comprises administering the cytokine drug (e.g., GM-CSF) or cytotoxic or cytostatic chemotherapeutic drug (e.g., cyclophosphamide) at the time of cancer vaccination. This can be achieved by, e.g., preparing the cancer vaccine in the suspension of the cytokine drug or cytotoxic or cytostatic chemotherapeutic drug.

In one embodiment, the method comprises administering the cytotoxic or cytostatic chemotherapeutic drug (e.g., cyclophosphamide, orally) or administering the cytokine drug (e.g., GM-CSF) following the cancer vaccination.

In one embodiment, the method comprises administering the cytokine drug (e.g., GM-CSF) at the time of cancer vaccination, and administering (e.g., intradermally) a same or different cytokine drug following the cancer vaccination.

In one embodiment, the method comprises administering the cytotoxic or cytostatic chemotherapeutic drugs (e.g., cyclophosphamide) at the time of cancer vaccination, and administering a same or different cytotoxic or cytostatic chemotherapeutic drug following the cancer vaccination.

In some instances, the method further comprises administering a therapeutically effective amount of a nucleic acid drug to the tumor or cancer.

In some instances, the method further comprises, post administration of the therapeutic composition, administering a cytokine drug (e.g., GM-CSF) or cytotoxic or cytostatic chemotherapeutic drug (e.g., cyclophosphamide) to the subject. The cytokine drug or cytotoxic or cytostatic chemotherapeutic drug can be administered subcutaneously.

In certain embodiments, the method comprises 1) preparing a cancer vaccine by ex vivo UV irradiation, exposure to low-dose GM-CSF or cyclophosphamide, and temperature-limited cryosurgical freezing of the cancerous tissue sample, 2) injecting the cancer vaccine lysate (e.g., intra-dermally) to the subject, 3) injecting two immunotherapeutic drugs (e.g., PD-1 inhibitor monoclonal antibody pembrolizumab (or nivolumab) and anti-CTLA-4 monoclonal antibody ipilimumab) (e.g., intra-dermally or intra-tumorally) to the subject, preferably at the same site, and 4) administering low-dose GM-CSF (e.g., subcutaneously) or low-dose cyclophosphamide (e.g., orally) to the subject for a period of time (e.g., 6 weeks).

As discussed above, the administration of the therapeutic composition or its components can be conducted via various routes, including but not limited to, administering orally or parenterally, such as intravenously, intramuscularly, subcutaneously, intra-tumorally, intra-orbitally, intra-capsularly, intra-peritoneally, intra-rectally, intra-cisternally, intra-vasally, intra-dermally; administering by passive or facilitated absorption through the skin using, for example, a skin patch, transdermal iontophoresis, or coated microneedles, respectively; administering to the site of a pathologic condition, for example, intravenously or intra-arterially into a blood vessel supplying a tumor; or combinations thereof.

The therapeutic composition or its components can be administered in an effective amount, at dosages, and for periods of time necessary to achieve the desired result. An effective amount can be administered in one or more administrations, applications or dosages. A therapeutically effective amount of a therapeutic composition (i.e., an effective dosage) depends on the therapeutic composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compositions described herein can include a single treatment or a series of treatments.

In some instances, the therapeutic composition is administered to the patient using an injection device. The injection device may comprise multiple tines or a single tine. The compositions can be administered using a probe (that serves different purposes) as described herein.

In some embodiments, the therapeutic compositions described herein can be administered in one or more administrations. These one or more administrations can be of the same or different methods of administration as described herein, for example, subcutaneously, intravenously, intramuscularly, intra-tumorally, intradermally, or any combinations thereof.

In some embodiments, a first composition (or its components) is administered intra-tumorally and a second composition (or its components) is administered subcutaneously. In some embodiments, a first and second compositions are administered simultaneously, in sequence, or in a series of treatments. In some embodiments, a first and the second compositions are the same, different, or the same in part. In some embodiments, the treatment methods include two or more administrations.

In some embodiments, a first administration is an intradermal administration of at least two checkpoint inhibitors (e.g., a PD-1 inhibitor and a CTLA-4 inhibitor), at least one cytokine or cytotoxic or cytostatic chemotherapeutic drug, and a cancer cell vaccine following ex vivo manipulation.

Dosage regimens can be adjusted to provide the desired therapeutic response. For example, several divided doses can be administered daily or the dose can be proportionally reduced as indicated by the exigencies of the therapeutic situation. Those skilled in the art will be aware of dosages and dosing regimens suitable for administration of the new monoclonal antibodies disclosed herein or antigen-binding fragments thereof to a subject. See e.g., Physicians' Desk Reference 2008 ($62^{nd}$ Ed., Thomson Reuters, 2008), which is incorporated herein by reference in its entirety. For example, dosage, toxicity, and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the treatment method, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The composition can be administered in a single dose or can be administered in more than one dose. The dosage ranges for the immune checkpoint inhibitors, the cytokine drugs or cytotoxic or cytostatic chemotherapeutic drugs, and the cancer vaccine have been discussed herein in the aspect of the therapeutic composition and are applicable in this aspect of the method of treating a tumor or a cancer in a subject.

In some embodiments, the composition is administered in a volume of less than about 1.0 ml. In some embodiments, the composition is administered in a volume of about 15 ml.

In some embodiments, the dosage of the immune checkpoint inhibitors, when measured based on the weight of the subject, can range from about 0.01 to about 10 mg/kg, for instance, from about 0.05 to about 10 mg/kg, from about 0.1 to about 10 mg/kg, from about 0.1 to about 5 mg/kg, from about 0.1 to about 3 mg/kg, from about 0.1 to about 2 mg/kg, from about 0.1 to about 1 mg/kg, or from about 0.5 to about 1 mg/kg.

In some embodiments, the dosage of the cytokine drugs, when measured based on the weight of the subject, can range from about 1 mg/kg to about 10 mg/kg, for instance, from about 1 mg/kg to about 10 mg/kg, from about 2 mg/kg to about 10 mg/kg, from about 2 mg/kg to about 5 mg/kg, from about 2 mg/kg to about 3 mg/kg, from about 2 mg/kg to about 2 mg/kg, from about 2 mg/kg to about 1 mg/kg, from about 2 to about 500 mg/kg, from about 2 to about 100 mg/kg, from about 2 to about 50 mg/kg, or from about 2 to about 10 mg/kg.

In some embodiments, the dosage of the cytotoxic or cytostatic chemotherapeutic drugs, when measured based on the weight of the subject, can range from about 1 µg/kg to about 10 mg/kg, for instance, from about 1 µg/kg to about 10 mg/kg, from about 2 µg/kg to about 10 mg/kg, from about 2 µg/kg to about 5 mg/kg, from about 2 µg/kg to about 3 mg/kg, from about 2 µg/kg to about 2 mg/kg, from about 2 µg/kg to about 1 mg/kg, from about 2 to about 500 µg/kg, from about 2 to about 100 µg/kg, from about 2 to about 50 µg/kg, or from about 2 to about 10 µg/kg.

In some instances, the cytokine drug or cytotoxic or cytostatic chemotherapeutic drug contained in the therapeutic composition may be administered at a dosage ranging from about 0.1 to about 1000 mg/m$^2$, for instance from about 10 to about 600 mg/m$^2$. In one embodiment, the cytokine drug or cytotoxic or cytostatic chemotherapeutic drug contained in the therapeutic composition is administered in a low dose, for instance less than about 500 mg/m$^2$, less than about 400 mg/m$^2$, or less than about 300 mg/m$^2$.

In one embodiment, the dose of the cytokine drug or cytotoxic or cytostatic chemotherapeutic drug contained in the therapeutic composition in each administration is about 0.25% to about 75% of its maximum tolerated dose after a traditional dosing regimen. For instance, the cytokine drug or cytotoxic or cytostatic chemotherapeutic drug contained in the therapeutic composition is administered in a low dosage that, the dose per administration is about 1%, about 5%, about 10%, about 15%, about 20%, about 25%, about 30%, about 35%, about 40%, about 45%, about 50%, about 55%, about 60%, about 65%, about 70%, or about 75%, of the maximum tolerated dose.

In some embodiments, the soft tissue administration of the therapeutic composition described herein produces fewer adverse side effects and/or immune-related adverse events, when compared to the conventional IV administration of the same composition. Adverse side effects and immune-related adverse events of conventional IV administration include gastrointestinal, respiratory, neurologic, endocrine, dermatologic, fatigue, renal, and hepatic effects.

In some embodiments, the administration of the therapeutic composition described herein produces fewer adverse side effects and/or immune-related adverse events in vivo, when compared to the administration of a same therapeutic composition comprising the at least two immune checkpoint inhibitors and the cytokine drug(s) or cytotoxic or cytostatic chemotherapeutic drug(s), without the ex vivo treated cancer vaccine, or when compared to the administration of a same therapeutic composition comprising the at least two immune checkpoint inhibitors and the ex vivo treated cancer vaccine, without the cytokine drug(s) or cytotoxic or cytostatic chemotherapeutic drug(s).

In some instances, the method further comprises a step of testing the location of a probe for soft tissue administration prior to administering the composition. The testing of the location of the probe can comprise administering a test injection via the probe and measuring the soft tissue pressure during administration of the test injection. In some instances, the method comprises re-locating the probe when increased or decreased soft tissue pressure is detected during the test injection as compared to pressure of the surrounding tumor tissue. For example, increased pressure can be indicative that the probe is within scar tissue and decreased pressure can be indicative that the probe is within a vessel.

During treatment, a skilled practitioner can use a system, e.g., a computer system, computational unit, software and/or algorithm; to plan, target, position, deliver, monitor, adjust, image, and/or test a treatment protocol. A skilled practitioner would understand that each injection method involves a number of parameters and variables that can be adjusted and could use an algorithm to control and design the injection. Any algorithm known in the art can be used in the methods described herein. Examples of computer systems, computational units, software and/or algorithms for use in manipulation techniques are known in the art.

Depending on the manipulation/irradiation methods used, the ex vivo manipulation/irradiation step can be carried out by the manipulation/irradiation techniques and systems known in the art. The discussions below provide non-limiting examples of various manipulation methods and devices.

For instance, cryosurgical freezing can be carried out by methods and devices described in PCT Application Publication Nos. WO 2004/086936 and WO 2008/142686; U.S. Pat. Nos. 6,074,412; 6,579,287; 6,648,880; 6,875,209; 7,220,257; and 7,001,378; all of which are incorporated herein by reference in their entirety. Exemplary devices include the Endocare™ CryoCare® series, for instance, CryoCare™ and CryoCare CN2 (HealthTronics, Inc., Austin, TX); CryoCor™ Cardiac Cryoablation System (CryoCor Inc.); Arctic Front® Cardiac CryoAblation Catheter System (Medtronic, Minneapolis, MN); Cryo Painblocker™ (Epi-Med, Dallas, TX).

Radio frequency (RF) manipulation can be carried out by methods and devices described in U.S. Pat. Nos. 5,246,438; 5,540,681; 5,573,533; 5,693,078; 6,932,814; and 8,152,801; all of which are incorporated herein by reference in their entirety.

Microwave manipulation can be carried out by methods and devices described in U.S. Pat. Nos. 6,325,796; 6,471,696; 7,160,292; 7,226,446; and 7,301,131; and U.S. Application Publication No. US 2003/0065317; all of which are incorporated herein by reference in their entirety.

Laser, photo, or plasma manipulation can be carried out by methods and devices described in U.S. Pat. Nos. 4,785,806; 5,231,047; 5,487,740; 6,132,424; 8,088,126; 9,204,918; and 10,023,858; and U.S. Application Publication No. US 2007/0129712; all of which are incorporated herein by reference in their entirety.

Ultrasound manipulation can be carried out by methods and devices described in U.S. Pat. Nos. 5,342,292; 6,821,274; 7,670,335; and 8,974,446; and U.S. Application Publication Nos. US 2006/0052706 and US 2009/00184; all of which are incorporated herein by reference in their entirety.

High-intensity focused ultrasound (HIFU) manipulation can be carried out by methods and devices described in U.S. Pat. Nos. 6,488,639; 6,936,046; 7,311,701; and 7,706,882; and U.S. Application Publication No. US 2008/0039746; all of which are incorporated herein by reference in their entirety.

Steam manipulation can be carried out by methods and devices described in U.S. Pat. Nos. 6,813,520 and 9,345,532; and U.S. Application Publication No. US 2013/0178910; all of which are incorporated herein by reference in their entirety.

Reversible electroporation (RE) manipulation can be carried out by methods and devices described in U.S. Application Publication Nos. US 2010/0023004 and US 2012/0109122; which are incorporated herein by reference in their entirety.

Irreversible electroporation (IRE) manipulation can be carried out by methods and devices described in U.S. Pat. Nos. 7,655,004 and 8,048,067; PCT Application Publication No. WO2012071526; and U.S. Application Publication Nos. US 2012/0109122 and US 2013/0253415; all of which are incorporated herein by reference in their entirety.

Radiofrequency electrical membrane breakdown manipulation can be carried out by methods and devices described in U.S. patent application US 2015/0150618, PCT Application Publication Nos. WO 2015/085162, WO 2016/123608, WO 2016/127162, WO 2016/126905, WO 2016/126778, and WO 2016/126811; which are incorporated herein by reference in their entirety.

Manipulation methods with ultra-short electrical pulse can be carried out by methods and devices described in U.S. Pat. No. 8,926,606; and U.S. Application Publication Nos. US 2006/0056480, US 2010/0261994, and US 2018/015414; all of which are incorporated herein by reference in their entirety. Exemplary devices include the Nano-Pulse Stimulation™ device (Pulse Biosciences, Inc., Hayward, CA).

Manipulation methods using photodynamic therapy can be carried out by methods and devices described in U.S. Pat. Nos. 6,811,562; 7,996,078; and 8,057,418; all of which are incorporated herein by reference in their entirety.

Manipulation methods using non-thermal shock waves can be carried out by methods and devices described in U.S. Pat. Nos. 5,524,620 and 8,556,813; U.S. Application Publication Nos. US 2016/0008016; and Japanese Application No. JP2009061083; all of which are incorporated herein by reference in their entirety.

Manipulation with chemical and/or biologics can be carried out by methods and devices described in U.S. Pat. No. 6,428,968; PCT Application Publication Nos. WO 2004/035110; WO 2006/095330, WO 2007/093036, and WO 2014/070820; and U.S. Application Publication Nos. US 2004/0002647, US 2005/0255039, US 2009/0192505, US 2010/0178684, US 2010/0145304, US 2012/0253192; US 2012/0046656, US 2016/0310200, and US 2016/0074626; all of which are incorporated herein by reference in their entirety.

The skilled artisan will appreciate that any parameters of the above manipulation techniques and devices can be modified as needed for ex vivo use and combined to achieve the desired manipulation. For instance, when it is desirable to combine cryosurgical freezing with RF-EMB manipulation, the methods and device can be modified or combined.

Additional descriptions relating to various devices that can combine cryosurgical freezing, electroporation, and/or RF-EMB are described in detail in PCT Application Publication No. WO 2017/123981, which is incorporated herein by reference in its entirety. More detailed description regarding using a multi-purpose probe as cryoprobes and/or electrodes are also described in WO 2017/123981.

As discussed above, the techniques or systems for carrying out ex vivo irradiation or radiation are well-known in the art, for laser radiation (e.g., ultraviolet or near infrared laser radiation), X-ray radiation, or gamma radiation.

As used herein, the term "nucleic acid drug" or "therapeutic nucleic acid" refers to a nucleotide, nucleoside, oligonucleotide or polynucleotide that is used to achieve a desired therapeutic effect. Exemplary nucleic acid drugs include, e.g., DNA, nDNA, mtDNA, gDNA, RNA, siRNA, miRNA, mRNA, piRNA, antisense RNA, snRNA, snoRNA, vRNA, etc. For example, the nucleic acid drug can be a DNA plasmid.

The term "subject" is used throughout the specification to describe an animal, human or non-human, to whom treatment according to the methods of the present invention is provided. Veterinary applications are clearly anticipated by the present invention. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs. The term "treat(ment)," is used herein to denote delaying the onset of, inhibiting, alleviating the effects of, or prolonging the life of a patient suffering from, a condition, e.g., cancer.

An "effective amount" is an amount sufficient to effect beneficial or desired results. For example, a therapeutically effective amount is one that achieves the desired therapeutic effect or to promote the desired physiological response. Effective amounts of compositions described herein for use in the present invention include, for example, amounts that enhance the immune response against tumors and/or tumor cells, improve the outcome for a patient suffering from or at risk for cancer, and improve the outcome of other cancer treatments. For cancer patients with a clinical response, the effective amount is sufficient to reduce, ameliorate, stabilize, reverse or slow the progression of the disease or other amount of reduction of pathological consequences of the disease. An effective amount can be administered in one or more administrations, applications or dosages. A therapeutically effective amount of a therapeutic composition (i.e., an effective dosage) depends on the therapeutic composition selected. A therapeutically effective amount of a therapeutic composition depends on the method of administration selected.

In some cases, intra-tumoral administration of a composition reduces the therapeutically effective amount of a composition, when compared to intravenous administration (e.g., conventional IV administration). The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compositions described herein can include a single treatment or a series of treatments.

A "cell line" or "cell culture" refers to cultures maintained in vitro or higher eukaryotic cells. It should be understood that progeny identical to the parent cell may (or morphologically, genotypically, or phenotypically).

The term "tumor cell" or "cancerous cell" used in the singular or plural form refers to malignant transformation so that it pathological cells of the host organism. Primary cancer cells (i.e., cells near the site of malignant transformation obtained) by well-established techniques, particularly histochemical examination and easily distinguished from non-cancerous cells. Cancer defined herein includes not only a primary cancer cell, but also any cell derived from a cancer cell ancestor. This includes metastasized cancer cells derived from cancer cells and in vitro cultures and cell lines.

The treatment methods described herein can be used alone or in combination with other methods for treating cancer in patients. Accordingly, in some instances, the methods described herein can further include treating the patient using surgery (e.g., to remove a portion of the tumor), chemotherapy, immunotherapy, gene therapy, and/or radiation therapy. Compositions and methods described herein can be administered to a patient at any point, e.g., before, during, and/or after the surgery, chemotherapy, immunotherapy, gene therapy, and/or radiation therapy.

The therapeutic compositions and treatment methods described herein are particularly useful for treating cancer in subjects. The term "cancer" refers to cells having the capacity for autonomous growth. Examples of such cells include cells having an abnormal state or condition characterized by rapidly proliferating cell growth. The term is meant to include cancerous growths, e.g., tumors; metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as many colon cancers, renal-cell carcinoma, prostate cancer and/or testicular tumors, non-small cell carcinoma of the lung, cancer of the small intestine, and cancer of the esophagus.

The therapeutic compositions and treatment methods described herein can be used to treat naturally arising cancer in a subject. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections.

Cancers to be treated with the therapeutic compositions and treatment methods described herein also include carcinomas, adenocarcinomas, sarcomas, and hematologic cancers. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "lymphoma" refers to malignant tumors of hematologic derivation.

Cancers or tumors that may be treated using the treatment methods and therapeutic compositions described herein include, for example, cancers or tumors of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck, thyroid, throat, and blood; sarcomas, choriocarcinomas, and lymphomas, among others. Exemplary tumors or cancers to be treated are cancers or tumors of prostate, pancreas, skin, colon, lung, and bladder.

Metastatic tumors or cancers (Stage IV) can be treated using the treatment methods and pharmaceutical compositions described herein. For example, performing a treatment method described herein on a tumor or cancer located at one site in the subject's body (e.g., a primary tumor), can stimulate the subject's immune defenses against the tumor or cancer and cause an immune attack on tumors or cancers of the same or even different type of at another site(s) in the subject's body (e.g., a metastatic tumor). A metastatic tumor or cancer can arise from a multitude of primary tumor or cancer types, including but not limited to, those of brain, prostate, colon, lung, breast, bone, peritoneum, adrenal gland, muscle, and liver origin. Metastases develop, e.g., when tumor cells shed from a primary tumor adhere to vascular endothelium, penetrate into surrounding tissues, and grow to form independent tumors at sites separate from a primary tumor.

Skilled practitioner will appreciate that the treatment methods and therapeutic compositions described herein can also be used to treat other stages of cancers or tumors, such as carcinoma in situ (stage 0), localized early stage cancer (stage I), and larger tumors or cancers (stage II and stage III).

Skilled practitioners will appreciate that the therapeutic compositions and treatment methods described herein can also be used to treat non-cancerous growths, e.g., noncancerous tumors. Exemplary non-cancerous growths include, e.g., benign tumors, adenomas, adenomyoeptheliomas, ductal or lobular hyperplasia, fibroadenomas, fibromas, fibrosis and simple cysts, adenosis tumor, hematomas, hamartomas, intraductal papillomas, papillomas, granular cell tumors, hemangiomas, lipomas, meningiomas, myomas, nevi, osteochondromas, phyllodes tumors, neuromas (e.g., acoustic neuromas, neurofibromas, and pyogenic granulomas), or warts (e.g., plantar warts, genital warts, flat warts, periungual warts, and filiform warts).

Skilled practitioners will appreciate that a subject can be diagnosed by a physician (or veterinarian, as appropriate for the subject being diagnosed) as suffering from or at risk for a condition described herein, e.g., cancer, by any method known in the art, e.g., by assessing a patient's medical history, performing diagnostic tests, and/or by employing imaging techniques.

As described herein, one exemplary method of treating a tumor in a patient comprises the steps of: (i) obtaining by biopsy or surgical resection a representative sample of the tumor or cancer within the patient; (ii) ex vivo manipulation/irradiation of at least a portion of the tumor or cancer; (iii) soft tissue administration of the therapeutic composition described herein to the tumor or cancer (e.g., a therapeutic composition comprising at least two immune checkpoint inhibitors and at least one cytokine or cytotoxic or cytostatic chemotherapeutic drug in combination with the autologous ex vivo manipulated cancer composition; and (iv) optionally administering a therapeutically effective amount of a nucleic acid drug to the tumor.

Also provided are kits that include one or more of the therapeutic compositions described herein. Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and/or instructions for use in a method described herein. In some cases the packaging contains a cartridge that can be controlled by a digital device following systematic instructions. Individuals skilled in the art can readily modify the packaging to suit individual needs.

In some embodiments, a kit provided herein can include at least one (e.g., one, two, three, four, five, or more) composition containing at least one (e.g., one, two, three, four, five, or more) of the compositions described herein, and at least one (e.g., one, two, three, four, five, or more) other composition in a separate vial containing a therapeutic or biologic agent known in the art to be effective in treating cancer.

Compositions and kits as provided herein can be used in accordance with any of the methods (e.g., treatment methods) described above. For example, compositions and kits can be used to treat cancer or tumor. Those skilled in the art will be aware of other suitable uses for compositions and kits provided herein, and will be able to employ the compositions and kits for such uses.

EXAMPLES

The following examples are for illustrative purposes only and are not intended to limit, in any way, the scope of the present invention.

Example 1—Treatment Regime

Treatment Regime with Cytokine Drug
Each treatment cycle involving a cytokine drug includes the following illustrative treatments:

Autologous cancer vaccine: intra-dermal (upper arm) or intra-tumoral injection of UV-irradiated autologous cancer lysate vaccine containing a minimum of 1 million lysed cancer cells, diluted in GM-CSF (Leukine) at a concentration of 250 mg/m$^2$, 1.0 ml total.

PD-1 inhibitor antibody pembrolizumab (Keytruda): intra-dermal or intra-tumoral injection into the same site, 0.5 ml.

Anti-CTLA-4 antibody ipilimumab (Yervoy): intra-dermal or intra-tumoral injection into the same site, 0.5 ml.

GM-CSF: subcutaneous administration, 250 mg daily for a total of about 6 weeks.

One or two additional treatment cycles can be taken as needed.

Treatment Regime with a Cytotoxic or Cytostatic Chemotherapeutic Drug
Each treatment cycle involving a cytotoxic or cytostatic chemotherapeutic drug includes the following illustrative treatments:

Autologous cancer vaccine: intra-dermal (upper arm) or intra-tumoral injection of UV-irradiated autologous cancer lysate vaccine containing a minimum of 1 million lysed cancer cells, diluted in cyclophosphamide (Cytoxan) at a concentration of 250 mg/m$^2$, 1.0 ml total.

PD-1 inhibitor antibody nivolumab (Opdivo): intra-dermal or intra-tumoral injection into the same site, 0.5 ml.

Anti-CTLA-4 antibody ipilimumab (Yervoy): intra-dermal or intra-tumoral injection into the same site, 0.5 ml.

Cyclophosphamide: oral administration, 25 mg twice a day or 50 mg once a day (2 weeks on, 2 weeks off, then 2 weeks back on beginning on the first day after treatment for a total of about 6 weeks).

One or two additional treatment cycles can be taken as needed.

Example 2—Preparation of Autologous Cancer Lysate Vaccine

Representative tumor tissue specimens (e.g., biopsy) and fine needle cellular aspirations are obtained by the local treating physician as per routine, immersed in saline, sealed in a sterile container.

All cancer lysate vaccine creation procedures are carried out in in accordance with Good Manufacturing Practices (GMP). Routine methods of handling are employed for each patient sample (e.g., standard operating procedures apply for shipping, receipt, and identification of laboratory specimens, processing requisition requirements, hazardous waste handling, etc.).

At the sterile pharmacy, the following processing steps are performed:

Tissue specimens are decanted of fluid and examined to determine the presence and extent of cancer. The tissues are then dissected by sterile scalpel to maximize the amount of cancer (by removing much of the non-cancerous tissue by dissection), and the relative percentages of the cancerous and non-cancer cells are estimated and recorded. The tissue is then minced finely, and a small amount is placed in a test tube and vortexed for 30 seconds. These steps are repeated to encompass the entire specimen. Tissue is then divided into 10 mg aliquots (approximate weight) in test tubes to ensure the presence in each of at least 1 million cancer cells.

Fine needle aspirates are quickly examined by light microscopy, and the relative percentages of the cancerous and non-cancer cells are estimated and recorded. The aspirate is then gently centrifuged at 1000 rpm for 1 minute to create a pellet of intact cells, supernatant is decanted, and the pellet is divided into 10 mg aliquots (approximate weight) in test tubes to ensure the presence of at least 1 million cancer cells.

Depending on the treatment regime in Example 1, each of the aliquots is diluted with GM-CSF (in 0.9% sterile sodium chloride), if the treatment regime involves a cytokine drug, or cyclophosphamide (reconstituted to 2% concentration (20 mg/ml)), if the treatment regime involves a cytotoxic or cytostatic chemotherapeutic drug.

This diluted aliquot is then treated to induce necroptosis (immunogenic cell death) with 300 mJ/cm$^2$ UV irradiation using a Stratalinker UV Crosslinker 1800 (Stratagene) and incubated in 5% $CO_2$ at 37° C. for 1 hour to allow necroptosis to proceed. Necrosis is then induced by 2 cycles of repetitive freezing (−40° C. dry ice/ethanol bath) and thawing (37° C. waterbath) cycles. In a third cycle, the aliquot is kept frozen on dry ice and shipped back to the treating physician where the final thaw (to room temperature) is performed immediately prior to patient injection in combination with the immunotherapeutic medications.

Example 3—Vaccine and Drug Delivery

Intra-Tumoral Injection

The operator draws the vial contents (the autologous cancer vaccine previously thawed immediately prior to injection and brought to room temperature; total of 1.0 ml) into a sterile syringe fitted with an 18 gauge, 1.5 inch drawing-up needle. The operator then attaches to the syringe an 18 gauge, 20 cm Chiba® biopsy needle (Cook Medical, Inc., Bloomington, Indiana).

The operator inserts the needle into the tumor under imaging guidance until the pre-determined location is reached by the needle tip, and then deposits the vaccine.

Leaving the needle in place, the operator removes the now-empty syringe and replaces it with a second syringe containing 1.0 ml of the first immunotherapeutic drug (anti-PD-1 antibodies), and deposits this drug throughout the area of prior injection with abundant overflow to include surrounding tissue in a manner identical to administration of the first injection.

The operator then repeats this procedure for a third syringe containing 1.0 ml of the second immunotherapeutic drug (anti-CTLA-4 antibodies), and deposits the third drug.

Intra-Dermal Injection

For preparation of intradermal injection of cancer vaccine, anti-PD-1 antibodies, or anti-CTLA-4 antibodies, the operator draws the vial contents (the autologous cancer vaccine previously thawed immediately prior to injection and brought to room temperature; total of 0.5 ml) into a sterile syringe fitted with an 18 gauge, 1.5 inch drawing-up needle. The operator then attaches to the syringe a ¼" to ½" long and 26 or 27 gauge thick needle. Alternatively, the operator may attach the syringe to an FDA-cleared microneedle (e.g., Micronjet 600, Nano Pass Technologies, Rehovat, Israel).

For administration of the cancer vaccine, the operator inserts the needle or microneedle into the skin. Regular-size needles employ the Mantoux Procedure, positioning the needle at angle of administration of 5 to 15 degrees, and injecting the syringe contents slowly and fully. Microneedles with attached cancer vaccine syringe are placed directly on the skin. The method of injection is the same for the anti-PD-1 antibodies and anti-CTLA-4 antibodies.

For administration of the anti-PD-1 antibodies and the anti-CTLA-4 antibodies, the operator inserts the needle or microneedle into the skin at the edge of the first wheal to allow intradermal contact of this fluid with that of the previously-administered cancer vaccine and antibodies. The method of injection is the same for the anti-PD-1 antibodies and anti-CTLA-4 antibodies.

Subcutaneous Administration of Low-Dose GM-CSF

For the treatment regime involving a cytokine drug as described in Example 1, the subcutaneous regimen of GM-CSF (Cy) at 250 mg daily is continued for 30 days for vaccine treatment.

Oral Metronomic Administration of Low-Dose Cyclophosphamide

For the treatment regime involving a cytotoxic or cytostatic chemotherapeutic drug as described in Example 1, the oral regimen of cyclophosphamide (Cy) at 25 mg b.i.d. (twice a day) or 50 mg q.d. (once a day) is continued for 14 days immediately following each treatment, followed by 14-day of no-drug administration, and a repeat of the oral administration for an additional 14 days.

What is claimed is:

1. A method of treating a tumor or a cancer in a subject in need consisting of:
   intradermally administering to the subject a therapeutic composition consisting of:
   i) two immune checkpoint inhibitors comprising a CTLA-4 inhibitor, and a PD-1 inhibitor or PD-L1 inhibitor,
   ii) cyclophosphamide, and
   iii) a cancer vaccine prepared from cancer cell lysates that have been prepared through an ex vivo treatment consisting of irradiation, cryofreezing, and suspension in a low-dose solution of cyclophosphamide, that creates necroptotic cancer cells while minimizing destruction of cancer antigens, in an amount effective to treat the tumor or cancer,
   wherein the cancer cell lysates are prepared by one or more treatments selected from the group consisting of dissociation or dissection, fixation, centrifugation, resuspension, enrichment, and combinations thereof; and post intradermal administration of the therapeutic composition, further administering a drug selected from a cytokine drug, a cytotoxic or cytostatic chemotherapeutic drug, and combinations thereof, to the subject daily.

2. The method of claim 1, wherein the drug is GM-CSF or cyclophosphamide.

3. The method of claim 1, wherein the drug is a cytokine drug administered subcutaneously or a cytotoxic or cytostatic chemotherapeutic drug administered orally.

4. The method of claim 1, wherein the therapeutic composition is administered to the subject's skin or soft tissue using an injection device.

5. The method of claim 1, wherein the concentration of the CTLA-4 inhibitor ranges from about 0.5 to about 10 mg/ml, and the concentration of the PD-1 or the PD-L1 inhibitor ranges from about 0.5 to about 20 mg/ml.

6. The method of claim 1, wherein the cancer cell lysates have been fixed by formalin, ethanol, or glutaraldehyde.

7. The method of claim 1, wherein the cryofreezing is carried out using a single probe, with total manipulating time of no more than 10 minutes.

8. The method of claim 1, wherein the cryofreezing is carried out at a temperature from about −35 to about −100° C.

9. The method of claim 1, wherein the cancer vaccine is autologous and the cancer cell lysates are from the subject being treated.

10. The method of claim 1, wherein the cancer vaccine is allogenic and wherein the cancer cell lysates are from cancer cell lines.

11. A method of treating a tumor or a cancer in a subject in need consisting of:
intradermally administering to the subject a therapeutic composition consisting of:
i) two immune checkpoint inhibitors comprising a CTLA-4 inhibitor, and a PD-1 inhibitor or PD-L1 inhibitor,
ii) cyclophosphamide, and
iii) a cancer vaccine prepared from cancer cell lysates that have been prepared through an ex vivo treatment consisting of irradiation, cryofreezing, and suspension in a low-dose solution of cyclophosphamide, that creates necroptotic cancer cells while minimizing destruction of cancer antigens, in an amount effective to treat the tumor or cancer,
wherein the cancer cell lysates are prepared by one or more treatments selected from the group consisting of dissociation or dissection, fixation, centrifugation, resuspension, enrichment, and combinations thereof.

12. The method of claim 11, wherein the therapeutic composition is administered to the subject's skin or soft tissue using an injection device.

13. The method of claim 11, wherein the concentration of the CTLA-4 inhibitor ranges from about 0.5 to about 10 mg/ml, and the concentration of the PD-1 or the PD-L1 inhibitor ranges from about 0.5 to about 20 mg/ml.

14. The method of claim 11, wherein the cancer cell lysates have been fixed by formalin, ethanol, or glutaraldehyde.

15. The method of claim 11, wherein the cryofreezing is carried out using a single probe, with total manipulating time of no more than 10 minutes.

16. The method of claim 11, wherein the cryofreezing is carried out at a temperature from about −35 to about −100° C.

17. The method of claim 11, wherein the cancer vaccine is autologous and the cancer cell lysates are from the subject being treated.

18. The method of claim 11, wherein the cancer vaccine is allogenic and wherein the cancer cell lysates are from cancer cell lines.

* * * * *